United States Patent
Sambelashvili et al.

(10) Patent No.: US 8,886,307 B2
(45) Date of Patent: Nov. 11, 2014

(54) ADAPTIVE CARDIAC RESYNCHRONIZATION THERAPY

(75) Inventors: Aleksandre T. Sambelashvili, Maple Grove, MN (US); Thomas J. Mullen, Andover, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 57 days.

(21) Appl. No.: 13/361,635

(22) Filed: Jan. 30, 2012

(65) Prior Publication Data

US 2013/0197599 A1 Aug. 1, 2013

(51) Int. Cl.
*A61N 1/368* (2006.01)

(52) U.S. Cl.
USPC ............................................................ 607/9

(58) Field of Classification Search
CPC ..... A61N 1/362; A61N 1/3622; A61N 1/365; A61N 1/3682; A61N 1/3684; A61N 1/371; A61N 1/3712
USPC ................................................ 607/9, 27, 28
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 6,871,096 B2 | 3/2005 | Hill | |
| 7,181,284 B2 | 2/2007 | Burnes | |
| 7,561,914 B2 | 7/2009 | Busacker et al. | |
| 7,706,879 B2 | 4/2010 | Burnes et al. | |
| 7,881,791 B2 | 2/2011 | Sambelashvili et al. | |
| 7,930,027 B2 | 4/2011 | Prakash et al. | |
| 7,941,218 B2 | 5/2011 | Sambelashvili et al. | |
| 2003/0083700 A1 | 5/2003 | Hill | |
| 2005/0209648 A1 | 9/2005 | Burnes et al. | |
| 2006/0287685 A1 | 12/2006 | Meyer et al. | |
| 2007/0191892 A1 | 8/2007 | Mullen et al. | |
| 2008/0269816 A1 | 10/2008 | Prakash et al. | |
| 2008/0269823 A1 | 10/2008 | Burnes et al. | |
| 2008/0280339 A1 | 11/2008 | KenKnight et al. | |
| 2008/0280341 A1 | 11/2008 | KenKnight et al. | |

(Continued)

FOREIGN PATENT DOCUMENTS

WO WO 2006/069032 A1 * 6/2006

OTHER PUBLICATIONS

Khaykin et al., "Adjusting the timing of left-ventricular pacing electrocardiogram and device electrograms," Europace doi:10.1093/europace/eur146, May 19, 2011, 7 pp.

(Continued)

*Primary Examiner* — George Evanisko
(74) *Attorney, Agent, or Firm* — Carol F. Barry

(57) ABSTRACT

Cardiac resynchronization therapy (CRT) delivered to a heart of a patient may be adjusted based on detection of a surrogate indication of the intrinsic atrioventricular conduction of the heart. In some examples, the surrogate indication is determined to be a sense event of the first depolarizing ventricle of the heart within a predetermined period of time following the delivery of a fusion pacing stimulus to the later depolarizing ventricle. In some examples, the CRT is switched from a fusion pacing configuration to a biventricular pacing configuration if the surrogate indication is not detected, and the CRT is maintained in a fusion pacing configuration if the surrogate indication is detected.

12 Claims, 12 Drawing Sheets

(56) References Cited

U.S. PATENT DOCUMENTS

| | | |
|---|---|---|
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2010/0016914 A1 | 1/2010 | Mullen et al. |
| 2010/0114232 A1 | 5/2010 | Min |
| 2010/0198291 A1 | 8/2010 | Sambelashvili et al. |
| 2010/0234916 A1 | 9/2010 | Turcott et al. |
| 2010/0286541 A1 | 11/2010 | Musley et al. |
| 2011/0190841 A1 | 8/2011 | Sambelashvili et al. |
| 2011/0196444 A1 | 8/2011 | Prakash et al. |

OTHER PUBLICATIONS (PCT/US2013/023411) Invitation to Pay Additional Fees and, Where Applicable, Protest Fee (6 pages) mailed May 8, 2013.

* cited by examiner

|  | LV-RV Conduction Peak R-Wave EGM Amplitude | AV Conduction Peak R-Wave EGM amplitude |  | LV-RV Conduction Peak R-Wave EGM Amplitude | AV Conduction Peak R-Wave EGM amplitude |
|---|---|---|---|---|---|
| Subj. 1 | 11 | 13 | Subj. 13 | 12 | 14 |
| Subj. 2 | 5.5 | 15 | Subj. 14 | 14 | BLOCK |
| Subj. 3 | 9 | BLOCK | Subj. 15 | 3.5 | 12 |
| Subj. 4 | 11.5 | 14 | Subj. 16 | 12 | 7 |
| Subj. 5 | 10 | 12 | Subj. 17 | 12 | BLOCK |
| Subj. 6 | 13 | 10 | Subj. 18 | 13 | 13 |
| Subj. 7 | 7 | BLOCK | Subj. 19 | 12 | 14.3 |
| Subj. 8 | 11 | 14 | Subj. 20 | 13 | 11 |
| Subj. 9 | 9 | 12 | Subj. 21 | 2.5 | 13 |
| Subj. 10 | 13 | BLOCK | Subj. 22 | 3 | 14 |
| Subj. 11 | 12 | 14.5 | Subj. 23 | 23 | 17 |
| Subj. 12 | 7 | 10.5 | Subj. 24 | 11.5 | 15 |

ADAPTIVE CARDIAC RESYNCHRONIZATION THERAPY

TECHNICAL FIELD

The disclosure relates to implantable medical devices, and, more particularly, to cardiac therapy delivery by implantable medical devices.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

Cardiac resynchronization therapy is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF).

SUMMARY

In general, the disclosure is directed to adaptive cardiac resynchronization (CRT) pacing therapy in which the type of pacing therapy (referred to herein as a "pacing configuration") is adjusted based on whether a surrogate indication of the presence of intrinsic atrioventricular conduction (also referred to as "intrinsic AV conduction") from an atrium of the heart to a first depolarizing ventricle is detected. The types of pacing therapies of the adaptive CRT may include, for example, fusion pacing and biventricular pacing, which may be delivered to a patient at different times. In some examples, the surrogate indication of intrinsic AV conduction includes a detection of ventricular activation of the first depolarizing ventricle ($V1_S$) of the heart within a predefined time window immediately following the delivery of a fusion pacing stimulus to the later depolarizing ventricle ($V2_P$). In some examples, the detected ventricular activation ($V1_S$) is confirmed to not be attributable to the fusion pacing stimulus ($V2_P$) prior to characterizing the ventricular activation ($V1_S$) as the surrogate indication of intrinsic AV conduction. A medical device may determine whether the surrogate indication of intrinsic AV conduction is detected on a beat-by-beat basis in some examples, and on a less frequent basis in other examples.

In some examples, the time interval between an atrial pace or sense event ($A_{P/S}$) and the an event (indicative of depolarization) sensed in the first depolarizing ventricle ($V1_S$) (within the predetermined window of time following the fusion pacing stimulus) may be periodically used to adjust the timing of the pacing stimuli, e.g., delivered to the later depolarizing ventricle ($V2_P$). For example, a fusion pacing interval may be adjusted based on the $A_{P/S}$–$V1_S$ interval.

In one example, the disclosure is directed to a system comprising an electrical stimulation module configured to deliver cardiac resynchronization pacing therapy to a heart of a patient, a sensing module, and a processor configured to control the electrical stimulation module to deliver a pacing stimulus to a first ventricle of a heart of a patient, and determine whether a surrogate indication of intrinsic conduction of the heart of the patient is detected after the electrical stimulation module delivers the pacing stimulus to the first ventricle. The processor is configured to determine whether the surrogate indication of the intrinsic conduction is detected by at least determining whether the sensing module detected activation of a second ventricle of the heart within a predetermined window of time immediately following delivery of the pacing stimulus to the first ventricle by the electrical stimulation module. In addition, the processor is configured to control the cardiac resynchronization therapy delivered by the electrical stimulation module to the patient based on whether the surrogate indication of intrinsic conduction is detected after the electrical stimulation module delivers the pacing stimulus to the first ventricle.

In another aspect, the disclosure is directed to a method comprising controlling an electrical stimulation module to deliver a pacing stimulus to a first ventricle of a heart of a patient, and, after the medical device delivers the pacing stimulus to the first ventricle, determining whether a surrogate indication of intrinsic conduction of the heart of the patient is detected. Determining whether the surrogate indication of intrinsic conduction is detected comprises detecting activation of a second ventricle of the heart within a predetermined window of time immediately following delivery of the pacing stimulus to the first ventricle. The method further comprises controlling cardiac resynchronization therapy delivered by the electrical stimulation module to the patient based on whether the surrogate indication of intrinsic conduction is detected.

In another aspect, the disclosure is directed to a system comprising means for delivering cardiac resynchronization therapy to a heart of a patient, and means for determining whether a surrogate indication of intrinsic conduction of the heart of the patient is detected after the means for delivering cardiac resynchronization therapy delivers a pacing stimulus to a first ventricle of the heart. The means for determining whether the surrogate indication of intrinsic conduction is detected comprises means for detecting activation of a second ventricle of the heart within a predetermined window of time immediately following delivery of the pacing stimulus to the first ventricle. The system further comprises means for controlling cardiac resynchronization therapy delivered by the means for delivering cardiac resynchronization therapy based on whether the surrogate indication of intrinsic conduction is detected.

In another aspect, the disclosure is directed to a computer-readable medium containing instructions. The instructions, when executed by a processor, cause the processor to control an electrical stimulation module to deliver a pacing stimulus to a first ventricle of a heart of a patient, and, after the medical device delivers the pacing stimulus to the first ventricle, determine whether a surrogate indication of intrinsic conduction of the heart of the patient is detected. The instructions cause the processor to determine whether the surrogate indication of the intrinsic conduction is detected by at least detecting activation of a second ventricle of the heart within a predetermined window of time immediately following delivery of the pacing stimulus to the first ventricle. The instructions also cause the processor to control cardiac resynchronization therapy delivered by the electrical stimulation module to the patient based on whether the surrogate indication of intrinsic conduction of the heart of the patient is detected.

In another aspect, the disclosure is directed to a computer-readable storage medium comprising computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The details of one or more examples are set forth in the accompanying drawings and the description below. Other features, objects, and advantages will be apparent from the description and drawings, and from the claims.

DETAILED DESCRIPTION

Figure 1:
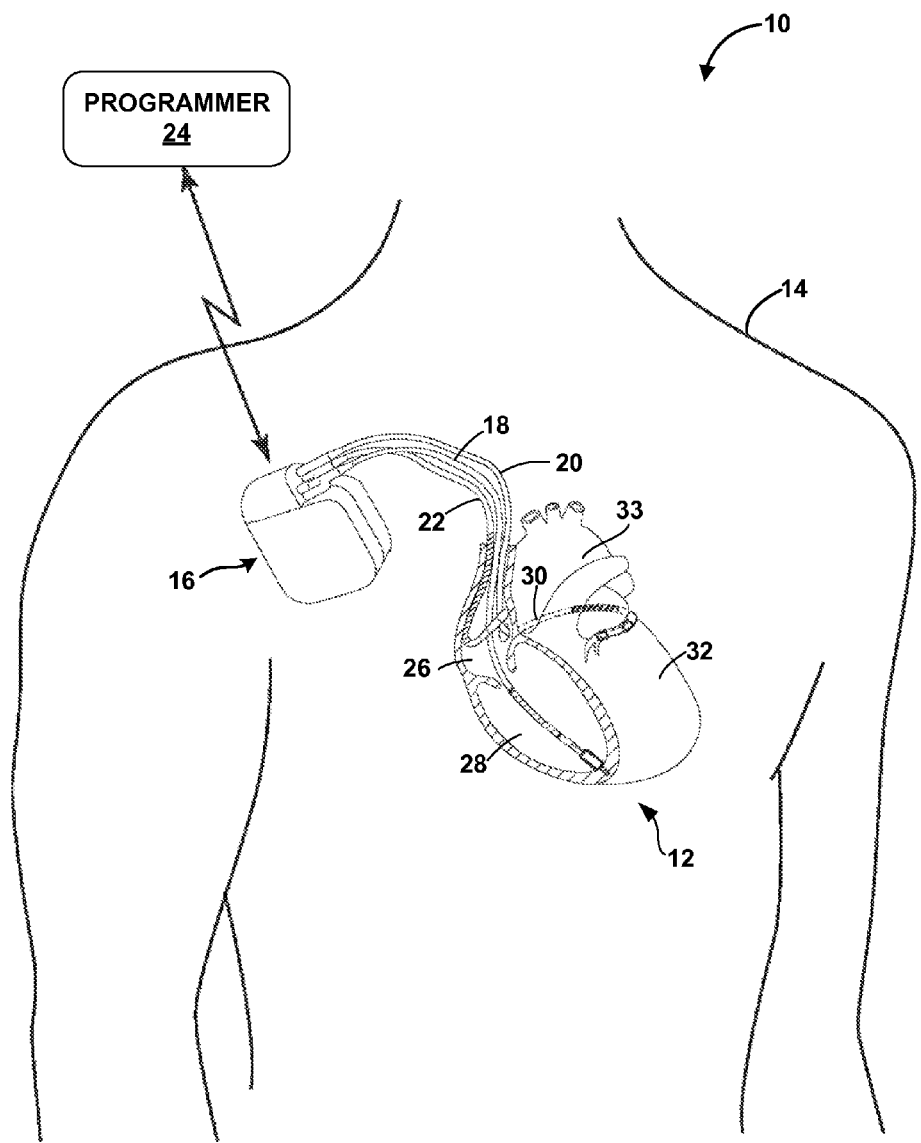
FIG. 1 is a conceptual diagram illustrating an example therapy system.

Devices, systems, and techniques for providing adaptive cardiac resynchronization (CRT) pacing are described herein. A medical device configured to provide adaptive CRT is configured to deliver pacing stimuli (e.g., pacing pulses) to the heart of the patient to resynchronize the electromechanical activity of the ventricles of the heart of a patient. The timing of the pacing stimuli may be controlled, e.g., by a processor, based on a pacing interval, which may be, for example, the duration of time following an atrial pace or sense event at which the pacing stimulus is delivered to the heart. Resynchronization of the electromechanical activity of the ventricles of the heart with the aid of CRT may be useful for patients with heart failure, or intraventricular or interventricular conduction delays (e.g., left or right bundle branch block).

In some proposed medical devices configured to provide adaptive CRT, a pacing configuration, e.g., a fusion pacing configuration (which may also be referred to as uni-ventricular fusion pacing) or a biventricular pacing configuration, and timing of the pacing stimuli based on periodic intrinsic conduction measurements may be periodically adjusted to achieve more efficient physiologic pacing and to improve hemodynamics of the patient. Fusion pacing and biventricular pacing are described in further detail below. While the pacing stimuli may be pacing pulses or continuous time signals, the pacing stimuli are primarily referred to herein as pacing pulses for ease of description.

Fusion-based cardiac resynchronization therapy (also referred to herein as fusion pacing) may be useful for restoring a depolarization sequence of a heart of a patient, which may be irregular due to ventricular dysfunction, in patients with preserved intrinsic atrial-ventricular (AV) conduction. In a fusion pacing configuration, a medical device delivers one or more fusion pacing pulses to a later-contracting ventricle (V2) in order to pre-excite the V2 and synchronize the depolarization of the V2 with the depolarization of the earlier contracting ventricle (V1). The ventricular activation of the V2 may "fuse" (or "merge") with the ventricular activation of the V1 that is attributable to intrinsic conduction of the heart. In this way, the intrinsic and pacing-induced excitation wave fronts may fuse together such that the depolarization of the V2 is resynchronized with the depolarization of the V1.

The medical device may be configured to deliver the fusion pacing pulse to the V2 according to a fusion pacing interval, which indicates the time relative to an atrial pace or sense event at which the fusion pacing pulse should be delivered to the V2. An atrial sense event may be, for example, a P wave of a sensed electrical cardiac signal and an atrial pacing event may be, for example, the time at which a stimulus is delivered to the atrium.

In some examples, the right ventricle (RV) may be the V1 and the left ventricle (LV) may be the V2. In other examples, the LV may be the V1 while the RV may be the V2. While the disclosure primarily refers to examples in which the first depolarizing ventricle V1 is the RV and the later depolarizing ventricle V2 is the LV, the devices, systems, techniques described herein for providing CRT may also apply to examples in which the first depolarizing ventricle V1 is the LV and the later depolarizing ventricle V2 is the RV.

In some fusion pacing techniques, a pacing pulse to the V2 ($V2_P$) is delivered upon expiration of a fusion pacing interval that is determined based on the intrinsic depolarization of the V1, which may be indicated by a sensing of ventricular activation ($V1_S$). Ventricular activation may be indicated by, for example, an R-wave of a sensed electrical cardiac signal. An example of a fusion pacing technique that times the delivery of the V2 pacing pulse ($V2_P$) to the intrinsic depolarization of the V1 is described in U.S. Pat. No. 7,181,284 to Burnes et al., which is entitled, "APPARATUS AND METHODS OF ENERGY EFFICIENT, ATRIAL-BASED BI-VENTRICU- LAR FUSION-PACING," and issued on Feb. 20, 2007. U.S. Pat. No. 7,181,284 to Burnes et al. is incorporated herein by reference in its entirety.

In one example disclosed by U.S. Pat. No. 7,181,284 to Burnes et al., a pacing pulse to the V2 ($V2_P$) is delivered a predetermined period of time following an atrial pace or sense event ($A_{P/S}$), where the predetermined period of time is substantially equal to the duration of time between the atrial pace or sense event ($A_{P/S}$) and a V1 sensing event ($V1_S$) of at least one prior cardiac cycle decremented by a duration of time referred to as the pre-excitation interval (PEI). Thus, one example equation that may be used to determine a fusion pacing interval ($A_{P/S}-V2_P$):

$$A_{P/S}-V2_P=(A_{P/S}-V1_S)-\text{PEI} \qquad \text{Equation (1)}$$

A cardiac cycle may include, for example, the time between the beginning of one heart beat to the next heartbeat. The duration of time between the atrial pace or sense event ($A_{P/S}$) and a V1 sensing event ($V1_S$) may be, for example, a measurement of intrinsic AV conduction time from an atrium to the first contracting ventricle of the heart of the patient. The PEI may indicate the amount of time with which a V2 pacing pulse precedes a V1 sensing event in order to achieve the fusing of the electromechanical performance of the V1 and V2. That is, the PEI may indicate the amount of time from the delivery of the V2 pacing pulse that is required to pre-excite the V2, such that the electromechanical performance of V1 and V2 merge into a fusion event. In some examples, the PEI is automatically determined by a medical device delivering the pacing therapy, e.g., based on determined intrinsic conduction times, while in other examples, the PEI may be predetermined by a clinician. In some examples, the PEI is a programmed value (e.g., about one millisecond (ms) to about 250 ms or more, such as about 100 ms to about 200 ms, or about 10 ms to about 40 ms) or is an adaptive value, such as about 10% of a measured intrinsic A-V2 conduction delay or measured intrinsic A-A cycle length.

The magnitude of the PEI may differ based on various factors, such as the heart rate of the patient, a dynamic physiologic conduction status of the heart of the patient, which may change based upon the physiological condition of the patient (e.g., ischemia status, myocardial infarction status, and so forth), as well as factors related to the therapy system, such as the location of sensing electrodes of the leads of the therapy system, the location of the pacing electrodes of the therapy system, and internal circuitry processing delays of the medical device.

Another technique for determining the timing of the delivery of a pacing pulse to a later depolarizing ventricle (V2) (which is sometimes also referred to as a "fusion pacing interval") is described in U.S. Patent Application Publication No. 2010/0198291 by Sambelashvili et al., which is incorporated herein by reference in its entirety. In some examples described by U.S. Patent Application Publication No. 2010/0198291 by Sambelashvili et al., the timing of the delivery of a pacing pulse is based on a depolarization of the V2 in at least one prior cardiac cycle. The depolarization of the V2 may be detected by sensing an event in the V2 ($V2_S$), such as an R-wave of an electrical cardiac signal. The V2 pacing pulse ($V2_P$) is timed such that an evoked depolarization of the V2 is effected in fusion with the intrinsic depolarization of the first depolarizing ventricle (V1), resulting in a ventricular resynchronization. In this way, the V2 pacing pulse ($V2_P$) may pre-excite the conduction delayed V2 and help fuse the activation of the V2 with the activation of the V1 from intrinsic conduction. The interval of time between the V2 pacing pulse ($V2_P$) and the V2 sensing event ($V2_S$) of the same cardiac cycle may be referred to as the adjusted PEI.

In some examples disclosed by U.S. Patent Application Publication No. 2010/0198291 by Sambelashvili et al., the predetermined period of time at which an IMD delivers the V2 pacing pulse ($V2_P$) following an atrial pace or sense event ($A_{P/S}$) is substantially equal to the duration of time between an atrial event (sensed or paced) ($A_{P/S}$) and a V2 sensing event ($V2_S$) of at least one prior cardiac cycle decremented by a duration of time referred to as an adjusted PEI. That is, in some examples, the adjusted PEI indicates the desired interval of time between the delivery of the V2 pacing pulse ($V2_P$) and the V2 sensing event ($V2_S$) of the same cardiac cycle. One example equation that may be used to determine the timing of a fusion pacing pulse using a technique described by U.S. Patent Application Publication No. 2010/0198291 by Sambelashvili et al. is:

$$A_{P/S}-V2_P\text{delay}=(A_{P/S}-V2_S)-\text{adjusted PEI} \qquad \text{Equation (2)}$$

The duration of time between an atrial pace or sense event ($A_{P/S}$) and a V2 sensing event ($V2_S$) may be referred to as an atrioventricular (AV) delay. The adjusted PEI may indicate an interval of time prior to a V2 sensing event ($V2_S$) at which it may be desirable to deliver the V2 pacing pulse ($V2_P$) in order to pre-excite the V2 and merge the electromechanical performance of V2 and V1 into a fusion event. In some examples described by U.S. Patent Application Publication No. 2010/0198291 by Sambelashvili et al., an adjusted PEI is a linear function that is based on V1 sensing event ($V1_S$) and a V2 sensing event ($V2_S$) of the same cardiac cycle, based on the time between an atrial pace or sense event ($A_{P/S}$) and a V2 sensing event, or any combination thereof.

As an example, adjusted PEI may be determined as follows:

$$\text{Adjusted PEI}=a(V1_S-V2_S)+b \qquad \text{Equation (3)}$$

According to U.S. Patent Application Publication No. 2010/0198291 by Sambelashvili et al., in Equation (3), the coefficients "a" and "b" may be fixed, empiric coefficients that are selected by a clinician or determined based on an adjusted PEI value selected by a clinician. In some examples, the coefficient "a" in Equation (3) may be about 1 and the coefficient "b" may be substantially equal to the PEI. In this case, the adjusted PEI is substantially equal to a time interval between a V1 sensing event ($V1_S$) and a V2 sensing event ($V2_S$) of the same cardiac cycle, incremented by the PEI. As a result, the $A_{P/S}-V2_P$ delay for timing the delivery of a V2 pacing pulse may be determined as follows $$A_{P/S}-V2_P\text{delay}=(A_{P/S}-V2_S)-[(V1_S-V2_S)+\text{PEI}] \qquad \text{Equation (4)}$$

Other values for the "a" and "b" coefficients in Equation (2) may be selected. In addition, other types of fusion pacing configurations may also be used in accordance with the techniques described herein. For example, other fusion pacing intervals described by U.S. Pat. No. 7,181,284 to Burnes et al. and U.S. Patent Application Publication No. 2010/0198291 by Sambelashvili et al. can also be used to control fusion pacing in accordance with techniques described herein. An example of CRT is described in U.S. Pat. No. 6,871,096 to Hill, which is entitled "SYSTEM AND METHOD FOR BI-VENTRICULAR FUSION PACING" and is incorporated herein by reference in its entirety.

In contrast to fusion pacing, in a biventricular pacing configuration, the medical device may deliver pacing pulses to both the LV and the RV in order to resynchronize the contraction of the LV and RV. In a biventricular pacing configuration, a medical device may deliver stimulation to coordinate contraction of the LV and the RV, even in the absence of intrinsic AV conduction of the heart.

In some proposed adaptive CRT pacing techniques, a pacing configuration (e.g., fusion pacing or biventricular pacing) and timing of the pacing pulses (e.g., a fusion pacing interval, such as a $A_{P/S}$–$V2_P$ delay, or biventricular pacing interval, such as a $V1_P$–$V2_P$ delay) are periodically adjusted based on periodic intrinsic conduction measurements in an attempt to achieve more efficient physiologic pacing and optimal hemodynamics. For example, some proposed cardiac rhythm management medical devices are configured to deliver adaptive CRT by delivering pacing to a heart of a patient in accordance with a fusion pacing configuration and, if loss of intrinsic AV conduction is detected (e.g., AV block), switching to a biventricular pacing configuration. Thus, a medical device configured for adaptive CRT may be configured to switch from a fusion pacing configuration to a biventricular pacing configuration in response to determining a heart of a patient is no longer intrinsically conducting. Biventricular pacing may consume more energy (compared to fusion pacing) due to the delivery of pacing to both the LV and the RV, and, accordingly, delivering fusion pacing until loss of intrinsic conduction may be a more efficient use of the power stored by a power source of a medical device compared to continuously delivering biventricular pacing.

In some existing proposed techniques for delivering adaptive CRT, a medical device switches from a fusion pacing configuration to a biventricular pacing configuration if the loss of intrinsic AV conduction is detected based on a measurement of intrinsic conduction time, which may be performed as part of the fusion-pacing interval determination. For example, loss of intrinsic AV conduction may be detected if a measured A–V1 conduction time ($A_{P/S}$–$V1_S$) is greater than (or greater than or equal to in some examples) a predetermined threshold value. In some examples, the predetermined threshold value is selected based on previous intrinsic conduction time intervals (e.g., may be a percentage of a mean or median of a certain number of prior intrinsic conduction time measurements). In other examples, the predetermined threshold value may be selected by a clinician to be, for example, a value that indicates the depolarization time of V1 that results maintenance of cardiac output at a desirable level.

Depending on the PEI used to time the fusion pacing pulses, in order to measure intrinsic conduction time, the pacing delivered by the medical device to the heart may be suspended to allow the heart of the patient to conduct in the absence of cardiac rhythm management therapy and to avoid interference between the delivery of pacing pulses and sensing of ventricular activation. In some examples, if pacing is delivered to an atrium of the heart, such pacing may be maintained, while pacing to the ventricles may be suspended. The measurement of intrinsic conduction time may be determined, e.g., as the time between an atrial pace or sense event ($A_{P/S}$) and a V1 sensing event ($V1_S$). The determinations of the intrinsic conduction time measurements may take place, for example, once a minute, once an hour, or once every 24 hours, although other frequencies may also be used.

The determinations of intrinsic conduction time may involve the suspension of some or all pacing therapy to the heart of the patient for at least one cardiac cycle, which may reduce the amount of synchronization of the ventricles of the heart during at least that one cardiac cycle. In addition, between the measurements of intrinsic conduction times, the intrinsic conduction times are assumed to stay constant. Further, if intrinsic conduction was detected during one measurement of intrinsic conduction time, the medical device is configured to assume that the heart is intrinsically conducting until the next intrinsic conduction time measurement, at which point the medical device may reassess intrinsic conduction. Accordingly, the pacing configuration of the medical device may only be switched as frequently as the intrinsic conduction time determinations are made.

If an abrupt complete AV block develops between two consecutive intrinsic conduction time measurements and is coupled with a loss of V2 pacing capture, a switch from the fusion pacing configuration to the biventricular pacing configuration may help minimize the possibility of a drop in the heart rate and cardiac output of the heart of the patient. However, in these existing proposed techniques for adaptive CRT, the switch to biventricular pacing configuration may not occur until the next intrinsic AV conduction time determination, which may be some time after the loss of intrinsic AV conduction and/or the loss of V2 capture by the medical device.

In comparison to these existing proposed techniques for delivering adaptive CRT, the devices, systems, and techniques described herein may provide a more responsive switch from a fusion pacing configuration to a biventricular pacing configuration when a loss of intrinsic AV conduction is present. As described herein, the devices, systems, and techniques described herein for providing adaptive CRT are directed to switching pacing configurations based on a surrogate indication of the presence or absence of intrinsic AV conduction, which is determined without the need to suspend delivery of electrical stimulation to the heart of the patient. The surrogate indication of intrinsic conduction may be used to verify V1 ventricular activation after, e.g., every paced beat or at least more frequently than the AV conduction time measurements. It may be desirable to confirm that the heart of the patient is intrinsically depolarizing in order to confirm that fusion pacing is still the proper pacing configuration for the patient. In some examples, the time delay between the atrial pace or sense event and the V2 sense event detected within the predetermined window of time following the pacing stimulus (V2), referred to herein as an $A_{P/S}$–$V1_S$ interval, may be used to as an AV conduction time that is used to adjust a pacing interval.

In some examples, while a medical device is delivering fusion pacing to a heart of a patient, the medical device may determine whether the heart is intrinsically conducting (e.g., from the right atrium to the first contracting ventricle V1) based on the surrogate indication of intrinsic AV conduction. In this way, the surrogate indication of intrinsic AV conduction may indicate whether a fusion pacing configuration is still appropriate for a patient. In some examples, the surrogate indication is determined to be a detection of ventricular activation ($V_{1S}$) of the first contracting ventricle (V1) within a predetermined window of time immediately following the delivery of a pacing stimulus to the later contracting ventricle ($V_{2P}$). The pacing stimulus ($V_{2P}$) may be, for example, a fusion pacing pulse that is delivered as part of fusion pacing therapy.

It is believed that the pacing stimulus ($V2_P$) may dissipate prior to propagating to the first contracting ventricle (V1), such that depolarization of the first contracting ventricle ($V1_S$) following the delivery of the pacing stimulus to the later contracting ventricle ($V2_P$) is attributable to intrinsic atrioventricular conduction, e.g., from the right atrium, left atrium, or both, via the atrioventricular (AV) node. As discussed in further detail below, e.g., with reference to FIGS. 7-11, the medical device may confirm that the sense event of the first contracting ventricle ($V1_S$) is not attributable to the pacing pulse that is delivered to the later contracting ventricle (V2$_P$), which may indicate the sense event of the other ventricle (V1$_S$) is attributable to intrinsic conduction. In some cases, a failure to detect the surrogate indication of intrinsic AV conduction for a certain number of beats may indicate a loss of intrinsic AV conduction.

If the medical device detects a loss of intrinsic AV conduction (e.g., because of a failure to detect the V1 ventricular activation after delivery of a pacing pulse to the V2 or a failure to detect the V1 ventricular activation for a certain number of beats), the medical device is configured to take one or more various responsive actions. In some examples, in response to detecting loss of intrinsic AV conduction based on the failure to detect the surrogate indication of intrinsic AV conduction, the medical device is configured to determine to suspend electrical stimulation to the heart and perform an intrinsic AV conduction time measurement in order to determine (e.g., verify) whether intrinsic AV conduction is present. The intrinsic AV conduction time measurement may include, for example, suspending or delaying all electrical stimulation to the ventricles of the heart of the patient and determining the time between an atrial pace or sense event (A$_{P/S}$) and activation of the first contracting ventricle (V1$_S$). In response to determining the intrinsic AV conduction time measurement indicates intrinsic AV conduction is present (e.g., that the V1 is activating in the absence of electrical stimulation to heart the heart), the medical device may maintain the fusion pacing configuration. On the other hand, in response to determining the intrinsic AV conduction measurement indicates intrinsic AV conduction is not present, the medical device may terminate the fusion pacing and switch to a biventricular pacing configuration.

In other examples, the medical device is configured to automatically terminate the fusion pacing and switch to a biventricular pacing configuration without performing an intrinsic AV conduction time determination if the medical device detects a loss of intrinsic AV conduction based on an absence of the surrogate indication of intrinsic AV conduction after the delivery of a fusion pacing pulse to the later depolarizing ventricle V2.

The techniques described herein for controlling adaptive CRT may be used with dual chamber or triple chamber medical devices, where sensing and pacing vectors are the same or different.

FIG. 1 is a conceptual diagram illustrating an example therapy system 10 that is configured to provide electrical stimulation therapy to heart 12 of patient 14. Therapy system 10 includes IMD 16, which is coupled to leads 18, 20, and 22, and programmer 24. IMD 16 may be, for example, an implantable pacemaker that provides electrical signals to heart 12 and senses electrical activity of heart 12 via electrodes coupled to one or more of leads 18, 20, and 22. In some examples, IMD 16 may include cardioversion and/or defibrillation capabilities.

Leads 18, 20, 22 extend into the heart 12 of patient 14 to sense electrical activity of heart 12 and deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lead 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., outside the vasculature of patient 14), such as epicardial electrodes, external surface electrodes, subcutaneous electrodes, and the like. In some examples, as described in further detail below, IMD 16 provides pacing pulses to heart 12 based on the electrical signals sensed within heart 12. For example, IMD 16 may provide pacing pulses to LV 32 based on the electrical signals sensed within RV 28. The configurations of electrodes used by IMD 16 for sensing and pacing may be unipolar or bipolar.

IMD 16 is configured to provide adaptive CRT to heart 12. In some examples, as part of the adaptive CRT, IMD 16 is configured to delivery at least one of fusion pacing to heart 12 and biventricular pacing therapy to heart 12. In some examples of fusion pacing, IMD 16 may deliver a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In this way, the pacing pulse delivered to LV 32 (LV$_P$) may pre-excite a conduction delayed LV 32 and help fuse the activation of LV 32 with the activation of RV 28 from intrinsic conduction. The fusion of the depolarization of LV 32 and RV 28 may result in synchronous activation and contraction of LV 32 with RV 28. In some examples, when IMD 16 is in a biventricular pacing configuration, IMD 16 may deliver a pacing stimulus (e.g., a pacing pulse) to RV 28 via electrodes of lead 18 and a pacing stimulus to LV 32 via electrodes of lead 20 in a manner that synchronizes activation and contraction of RV 28 and LV 28.

As discussed in further detail below, in some examples, IMD 16 may be configured to adapt the pacing configuration to the cardiac status of heart 12 by delivering electrical stimulation therapy to heart 12 according to the fusion pacing configuration and, when an absence of intrinsic AV conduction (e.g., from RA 26 to RV 28) is detected, adjust a pacing parameter, e.g., by switching to a biventricular pacing configuration or another multisite pacing, or increasing the pacing output (e.g., the frequency of pacing pulses or the intensity of the pacing pulses, such as the current or voltage amplitude). While IMD 16 may periodically measure intrinsic AV conduction times to confirm the presence of intrinsic AV conduction, IMD 16 may more frequently determine that intrinsic AV conduction is absent based on surrogate indication of the intrinsic AV conduction time of heart 12. In this way, the surrogate indication of intrinsic AV conduction may indicate whether a fusion pacing configuration is still appropriate for a patient.

The surrogate indication is not an actual measurement of intrinsic AV conduction time, but is an indication that RV 28 has intrinsically activated. The surrogate indication may be an occurrence of ventricular sense event of RV 28 (RV$_S$), which indicates activation of RV 28, within a predetermined window of time (e.g., about 30 milliseconds to about 100 milliseconds) after delivery of a pacing pulse to LV 32 (LV$_P$). The ventricular sense event of RV 28 can be, for example, an R-wave of an electrical cardiac signal sensed via electrodes of lead 18. If the blanking interval with which IMD 16 senses electrical cardiac activity of heart 12 following the LV pace event (LV$_P$) is greater than the predetermined window of time, the blanking window may be shortened in some examples in order to detect the surrogate indication of the intrinsic AV conduction. In some examples, IMD 16 determines a time delay between the time IMD 16 delivers a pacing pulse to LV 32 (LV$_P$) and a subsequent sense event of RV 28 (RV$_S$).

In some cases, the electrical activation of LV 32 caused by delivery of the pacing pulse to LV 32 (LV$_P$) may propagate to RV 28, and may present itself in an electrical cardiac signal (e.g., an electrocardiogram (ECG) or cardiac electrogram (EGM)) as an RV sense event RV$_S$, and, therefore, the RV sense event RV$_S$ may not be representative of intrinsic AV conduction. In order to confirm that the RV sense event RV$_S$ is representative of intrinsic AV conduction, IMD 16 may confirm that the sense event of RV 28 (RV$_S$) is not attributable to the pacing pulse is delivered to LV 32 (LV$_P$). Example techniques for confirming that the sense event of RV 28 (RV$_S$) is not attributable to the pacing pulse is delivered to LV 32 (LV$_P$) are described in further detail below with reference to FIGS. 7-11.

The adaptive CRT provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 26. The depolarization wave is transmitted through the atrial conduction pathways of Bachmann's Bundle and the Internodal Tracts at the atrial level into the LA 33 septum. When the atrial depolarization wave has reached the AV node, the atrial septum, and the furthest walls of the right and left atria 26, 33, respectively, the atria 26, 33 may contract as a result of the electrical activation. The aggregate right atrial and left atrial depolarization wave appears as the P-wave of the PQRST complex of an electrical cardiac signal, such as an EGM or ECG. When the amplitude of the atrial depolarization wave passing between a pair of unipolar or bipolar pace/sense electrodes located on or adjacent RA 26 and/or LA 33 exceeds a threshold, it is detected as a sensed P-wave. The sensed P-wave may also be referred to as an atrial sensing event, or an RA sensing event (RA$_S$). Similarly, a P-wave sensed in the LA 33 may be referred to as an atrial sensing event or an LA sensing event (LA$_S$).

During or after the atrial contractions, the AV node distributes the depolarization wave inferiorly down the Bundle of His in the intraventricular septum. The depolarization wave may travel to the apical region of heart 12 and then superiorly though the Purkinje Fiber network. The aggregate right ventricular and left ventricular depolarization wave and the subsequent T-wave accompanying re-polarization of the depolarized myocardium may appear as the QRST portion of the PQRST cardiac cycle complex. When the amplitude of the QRS ventricular depolarization wave passing between a bipolar or unipolar pace/sense electrode pair located on or adjacent RV 28 and/or LV 32 exceeds a threshold, it is detected as a sensed R-wave. The sensed R-wave may also be referred to as a ventricular sensing event, an RV sensing event (RV$_S$), or an LV sensing event (LV$_S$) depending upon the ventricle in which the electrodes of one or more of leads 18, 20, 22 are configured to sense in a particular case.

Some patients, such as patients with congestive heart failure or cardiomyopathies, may have left ventricular dysfunction, whereby the normal electrical activation sequence through heart 12 is compromised within LV 32. In a patient with left ventricular dysfunction, the normal electrical activation sequence through the heart of the patient becomes disrupted. For example, patients may experience an intra-atrial conduction defect, such as intra-atrial block. Intra-atrial block is a condition in which the atrial activation is delayed because of conduction delays between RA 26 to LA 33.

As another example, a patient with left ventricular dysfunction may experience an interventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either RV 28 or LV 32 is delayed with respect to the other ventricle, causing asynchrony between the depolarization of the right and left ventricles. Ventricular asynchrony may be identified by a widened QRS complex due to the increased time for the activation to traverse the ventricular conduction paths. The asynchrony may result from conduction defects along the Bundle of His, the Right and Left Bundle Branches or at the more distal Purkinje Terminals. Typical intra-ventricular peak-to-peak asynchrony can range from about 80 ms to about 200 ms or longer. However, in patients who are experiencing RBBB and LBBB, the QRS complex may be widened far beyond the normal range to a wider range, e.g., about 120 ms to about 250 ms or greater.

CRT delivered by IMD 16 may help alleviate heart failure conditions by restoring synchronous depolarization and contraction of one or more chambers of heart 12. In some cases, the fusion pacing of heart 12 described herein enhances stroke volume of a patient by improving the synchrony with which RV 28 and LV 32 depolarize and contract.

The duration of a cardiac cycle of heart 12, which includes the depolarization-repolarization sequence, may change depending on various physiological factors of patient 14, such as a heart rate. As heart rate of patient 14 changes, the timing of the delivery of a pacing pulse to LV 32 (LV$_P$) during fusion pacing therapy or the timing of the delivery of pacing pulses to RV 28 (RV$_P$) and LV 32 (LV$_P$) during biventricular pacing therapy may change. Accordingly, when IMD 16 is delivering fusion pacing to heart 12, it may be useful for IMD 16 to periodically adjust a fusion pacing interval in order to maintain the delivery of the LV 32 pacing pulse (LV$_P$) at a time that results in a fusion of the depolarization of LV 32 and RV 28. In addition, when IMD 16 is delivering biventricular pacing therapy to heart 12, it may be useful for IMD 16 to periodically evaluate a biventricular pacing interval in order to maintain the delivery of the LV 32 pacing pulse (LV$_P$) at a time relative to the RV 28 pacing pulse (RV$_P$) that results in a synchrony of contraction of LV 32 and RV 28. As discussed in further detail below, in some examples, IMD 16 adjusts the fusion pacing interval based on the A$_{P/S}$–RV$_S$ interval of a cardiac cycle, where the RV sense event (RV$_S$) is sensed within the predetermined window of time immediately following the LV 32 pacing pulse (LV$_P$).

In some examples, IMD 16 delivers pacing pulses to LV 32 until a loss of capture occurs in LV 32. Depolarization of the myocardial cells in response to a pacing pulse may be referred to as "capture." Detection of loss of capture in LV 32 may indicate that the LV pacing pulse (LV$_P$) is being delivered too late (e.g., during the refractory period of LV 32) or that the LV 32 pacing electrodes have become dislodged or lead 20 has a lead-related condition (e.g., comprised insulation or a fracture). If the loss of capture is detected, e.g., by a failure to detect an LV sensing event (LV$_S$) within a predetermined amount of time following the delivery of a LV pacing pulse, IMD 16 may discontinue the fusion pacing therapy. In some cases, IMD 16 switches to a different pacing mode (e.g., an AAI, ADI, AAI/R, ADI/R, double chamber DDD or DDD/R, and the like) after discontinuing the fusion pacing therapy.

In some examples, IMD 16 also provides defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 is programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as sensed electrical activity, intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
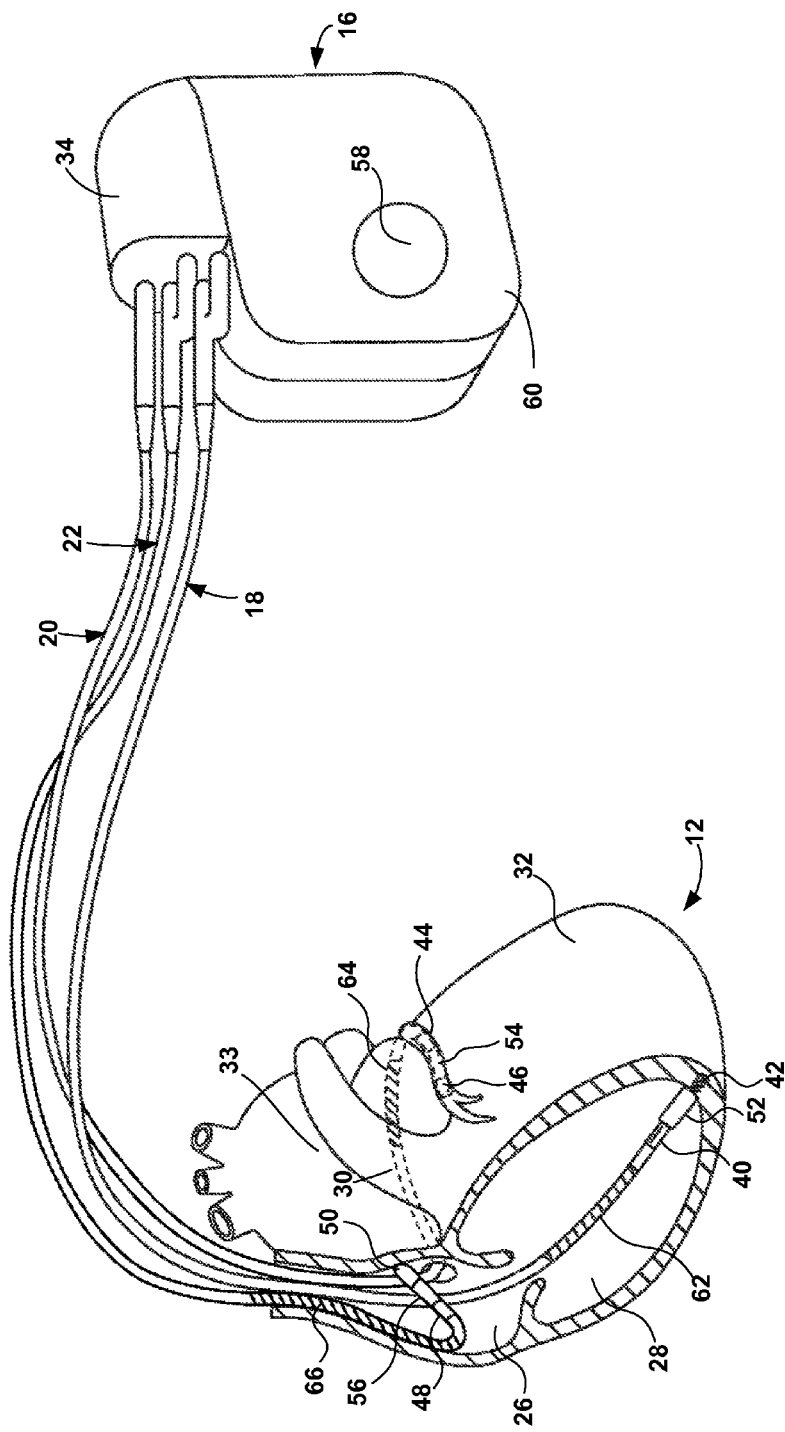
FIG. 2 is a conceptual diagram illustrating the medical device and leads of the therapy system of FIG. 1 in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. As described in further detail with reference to FIG. 3, housing 60 may enclose a stimulation generator that generates cardiac pacing pulses and defibrillation or cardioversion shocks, as well as a sensing module for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include extravascular electrodes, such as subcutaneous electrodes, epicardial electrodes, and/or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

Figure 3:
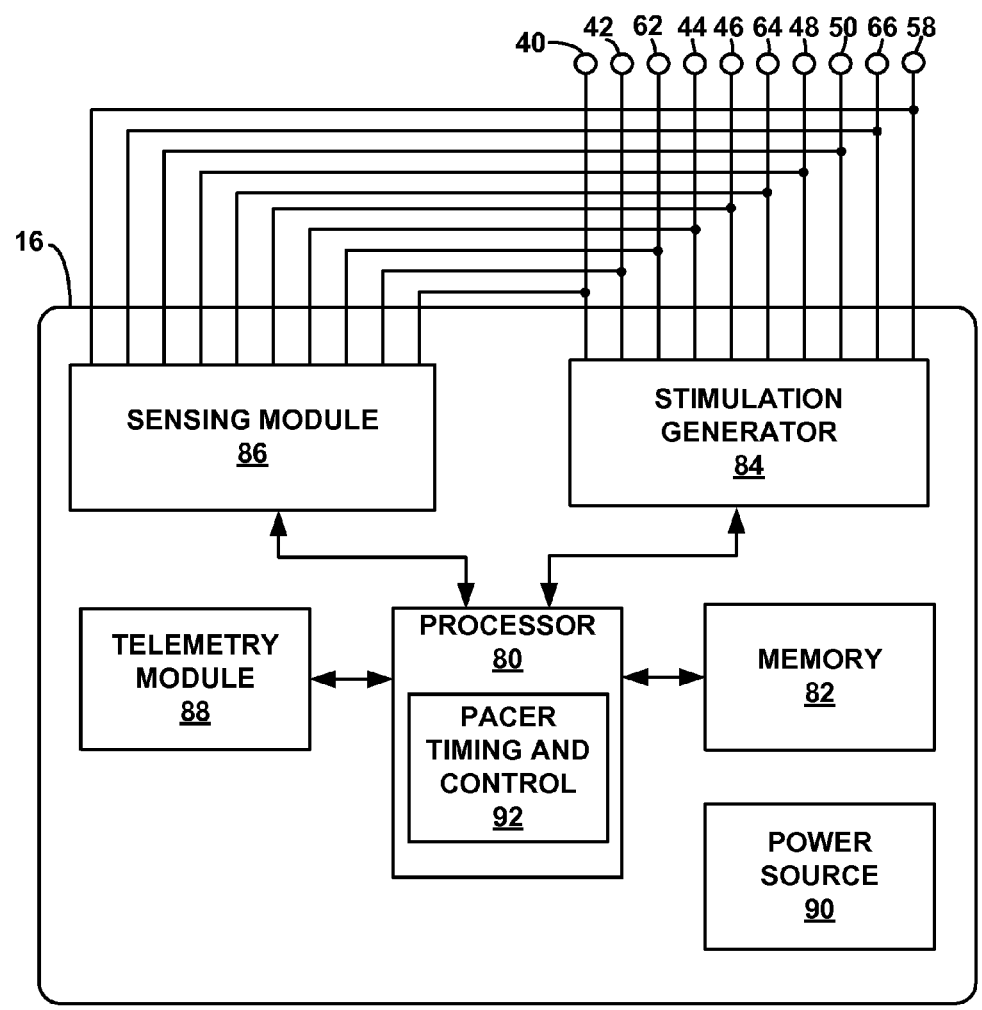
FIG. 3 is a functional block diagram of an example implantable medical device that delivers stimulation to a heart of a patient.

In other examples of therapy systems that provide electrical stimulation therapy to heart 12, a therapy system may include any suitable number of leads coupled to IMD 16, and each of the leads may extend to any location within or proximate to heart 12. For example, a therapy system may include a single chamber or dual chamber device rather than a three-chamber device as shown in FIG. 1. In a single chamber configuration, IMD 16 is electrically connected to a single lead 20 that includes stimulation and sense electrodes within LV 32. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RA 28 and LV 32. Other lead configurations are contemplated.

FIG. 3 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more time intervals for timing fusion pacing therapy and biventricular pacing therapy to heart 12 (e.g., PEI values, adjusted PEI values, biventricular pacing intervals, or any combination thereof) may be stored by memory 82.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 is configured to control stimulation generator 84 to deliver stimulation therapy to heart 12 according to a selected one or more of therapy programs, which may be stored in memory 82. For example, processor 80 may be configured to stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy. For example, stimulation generator 84 may deliver a pacing stimulus to LV 32 (FIG. 2) of heart 12, e.g., in accordance with the fusion pacing techniques described herein, via at least two electrodes 44, 46 (FIG. 2). As another example, stimulation generator 84 may deliver a pacing stimulus to RV 28 via at least two electrodes 40, 42 (FIG. 2) and a pacing stimulus to LV 32 via at least two electrodes 44, 46 (FIG. 2), e.g., in accordance with the biventricular pacing techniques described herein.

In some examples, stimulation generator 84 is configured to deliver cardioversion or defibrillation shocks to heart 12. The pacing stimuli, cardioversion shocks, and defibrillation shocks may be in the form of stimulation pulses. In other examples, stimulation generator may deliver one or more of these types of stimulation in the form of other signals, such as sine waves, square waves, or other substantially continuous time signals.

Stimulation generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, processor 80 may select a subset of electrodes 40, 42, 44, 46, 48, 50, 58, 62, 64, and 66 with which stimulation is delivered to heart 12 without a switch module.

Sensing module 86 is configured to monitor signals from at least one of electrodes 40, 42, 44, 46, 48, 50, 58, 62, 64 or 66 in order to monitor electrical activity of heart 12, e.g., via EGM signals. For example, sensing module 86 may sense atrial events (e.g., a P-wave) with electrodes 48, 50, 66 within RA 26 or sense an LV 32 event (e.g., an R-wave) with electrodes 44, 46, 64 within LV 32. In some examples, sensing module 86 includes a switch module to select which of the available electrodes are used to sense the heart activity. For example, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in RA 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

Signals generated by sensing module 86 may include, for example: an RA-event signal, which indicates a detection of a P-wave via electrodes implanted within RA 26 (FIG. 1); an LA-event signal, which indicates a detection of a P-wave via electrodes implanted within LA 33 (FIG. 1); an RV-event signal, which indicates a detection of an R-wave via electrodes implanted within RV 28; or an LV-event signal, which indicates a detection of an R-wave via electrodes implanted within LV 32. In the example of therapy system 10 shown in FIGS. 1 and 2, IMD 16 is not connected to electrodes that are implanted within LA 33. However, in other example therapy systems, IMD 16 may be connected to electrodes that are implanted within LA 33 in order to sense electrical activity of LA 33.

Processor 80 may define variable intervals for timing the delivering of pacing pulses to heart 12 based on one or more signals sensed by sensing module 86. For example, processor 80 may define variable intervals for timing the delivery of LV fusion pacing pulses ($LV_P$) based on signals from sensing module 86. These intervals may include, for example, a fusion pacing interval (e.g., $A_{P/S}$-$LV_P$ delay or $LV_P$-$LV_S$ delay) and intervals used to determine the fusion pacing intervals or other pacing intervals (e.g., $A_{P/S}$-$LV_S$, $RV_S$-$LV_S$, or $LV_S$-$LV_S$). Example techniques for determining the fusion pacing intervals ($A_{P/S}$-$LV_P$) is described in U.S. Pat. No. 7,181,284 to Burnes et al. and U.S. Patent Application Publication No. 2010/0198291 by Sambelashvili et al. As another example, processor 80 may define variable intervals for timing the delivery of RV 28 and LV 32 pacing pulses during the delivery of biventricular pacing therapy based on one or more signals sensed by sensing module 86. These intervals may include, for example, an interval for pacing RV 28 relative to an atrial pace or sense event (e.g., the $A_{P/S}$-$RV_P$ delay) or an interval for pacing LV 32 relative to the RV 28 pace event (e.g., the $RV_P$-$LV_P$ delay).

Processor 80 includes pacer timing and control module 92, which may be embodied as hardware, firmware, software, or any combination thereof. Pacer timing and control module 92 may comprise a dedicated hardware circuit, such as an ASIC, separate from other processor 80 components, such as a microprocessor, or a software module executed by a component of processor 80 (e.g., a microprocessor or ASIC). Pacer timing and control module 92 may help define the pacing interval (e.g., $A_{P/S}$-$LV_P$ delay, $LV_S$-$LV_P$ delay, $A_{P/S}$-$RV_P$ delay, or the $RV_P$-$LV_P$ delay) for controlling the delivery of a pacing pulse to LV 32. For example, pacing timing and control module 92 may include programmable counters or timers for determining the $A_{P/S}$-$LV_P$ delay, the $LV_S$-$LV_P$ delay, and/or any other relevant time intervals. In addition, pacing timing and control module 92 may include timers for timing the delivery of pacing pulses and other functions that are based on the pacing interval.

For example, in examples of fusion pacing in which IMD 16 delivers the LV pacing pulse ($LV_P$) a predetermined period of time following an atrial pace or sense event ($A_{P/S}$), pacing timing and control module 92 may include a timer that is loaded with the appropriate $A_{P/S}$-$LV_P$ delay. The timer of pacing timing and control module 92 may be configured to begin upon the detection of a preceding atrial pace or sense event ($A_{P/S}$). Upon expiration of the particular timer, processor 80 may control stimulation generator 84 to deliver pacing stimulus $LV_P$ to LV 32. For example, pacing timing and control module 92 may generate a trigger signal that triggers the output of a pacing pulse by stimulation generator 84.

As another example, in some examples of fusion pacing in which IMD 16 delivers the LV pacing pulse ($LV_P$) a predetermined period of time following a LV 32 sensing event ($LV_S$), pacing timing and control module 92 may include a timer that is loaded with the appropriate $LV_S$-$LV_P$ delay. The timer of pacing timing and control module 92 may be configured to begin upon detection of a preceding LV sensing event ($LV_S$). Upon expiration of the particular timer, processor 80 may control stimulation generator 84 to deliver pacing stimulus $LV_P$ to LV 32 (FIG. 1).

In some examples of biventricular pacing in which IMD 16 delivers a pacing pulse to RV 28 a predetermined period of time following an atrial pace or sense event ($A_{P/S}$), pacing timing and control module 92 may include a timer that is loaded with the appropriate $A_{P/S}$-$RV_P$ delay. The timer of pacing timing and control module 92 may be configured to begin upon detection of a preceding atrial pace or sense event ($LV_S$). Upon expiration of the particular timer, processor 80 may control stimulation generator 84 to deliver pacing stimulus $RV_P$ to RV 28 (FIG. 1). In addition, in some examples of biventricular pacing in which IMD 16 delivers a pacing pulse to LV 28 a predetermined period of time following right ventricular pacing event ($RV_P$), pacing timing and control module 92 may include a timer that is loaded with the appropriate $RV_P$-$LV_P$ delay. The timer of pacing timing and control module 92 may be configured to begin upon detection of a RV pacing event ($RV_P$). Upon expiration of the particular timer, processor 80 may control stimulation generator 84 to deliver pacing stimulus $LV_P$ to LV 32 (FIG. 1).

In examples in which IMD 16 is configured to deliver other types of cardiac rhythm therapy in addition to fusion pacing and biventricular pacing, pacer timing and control module 92 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to excitation fusion pacing, intervals defined by pacer timing and control module 92 within processor 80 may include atrial and ventricular pacing escape intervals, refractory periods during which sensed P-waves and R-waves are ineffective to restart timing of the escape intervals, and the pulse widths of the pacing pulses. As another example, pacer timing and control module 92 may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing modes other than the fusion pacing, escape interval counters within pacer timing/control module 92 of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including fusion cardiac resynchronization therapy.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processor 80 may operate as an interrupt driven device, and is responsive to interrupts from pacer timing and control module 92, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

If IMD 16 is configured to generate and deliver defibrillation pulses to heart 12, stimulation generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module (not shown), which may, like pacer timing and control module 92, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., EGM signals) produced by atrial and ventricular sense amp circuits within sensing module 86 to programmer 24. Other types of information may also be transmitted to programmer 24, such as the various intervals and delays used to deliver the fusion pacing pulse to LV 32. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 4:
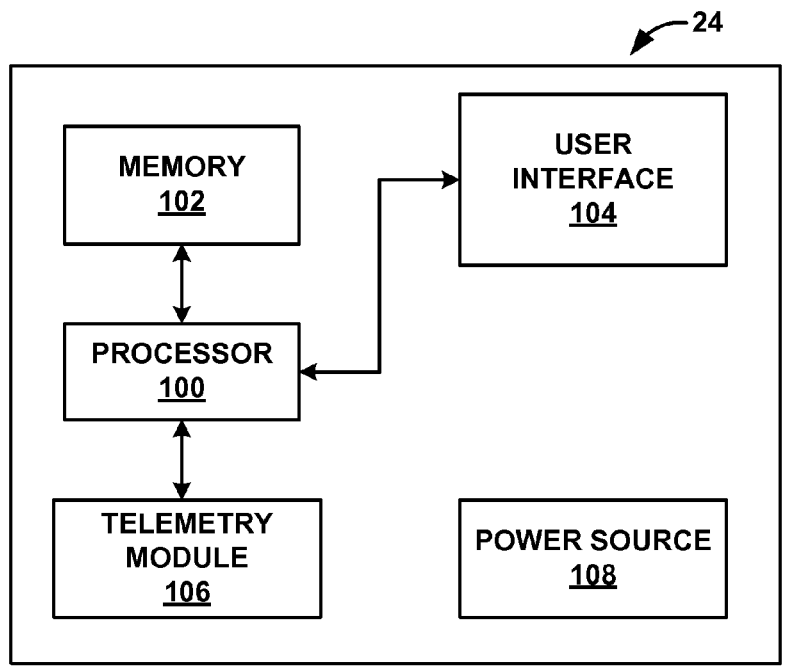
FIG. 4 is a functional block diagram of an example medical device programmer.

FIG. 4 is block diagram of an example programmer 24. As shown in FIG. 4, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1.

Telemetry module 106 may be similar to telemetry module 88 of IMD 16 (FIG. 3). Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 is configured to deliver operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Example techniques that IMD 16 may implement in order to deliver adaptive CRT are described with respect to FIGS. 5-12. FIGS. 5-11 illustrate example techniques for selecting a pacing configuration for adaptive CRT based on a surrogate indication of intrinsic AV conduction of heart 12. FIG. 13 illustrates an example technique for adjusting a fusion pacing interval based on at least one $A_{P/S}$–$RV_S$ interval. While FIGS. 5-12 are primarily described as being performed by processor 80 of IMD 16, in other examples, a processor of another device, such as processor 100 of programmer 24, may perform any part of the techniques described herein, including those described with respect to FIGS. 5-12.

Figure 5:
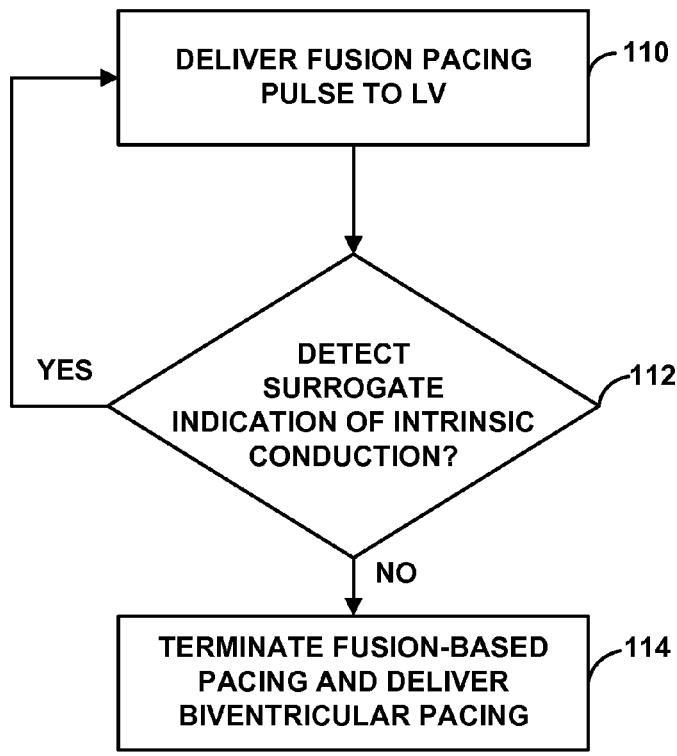
FIGS. 5 and 6 are flow diagrams of example techniques for providing adaptive cardiac resynchronization therapy based on a surrogate indication of the presence of intrinsic AV conduction.

FIG. 5 is a flow diagram of an example technique that IMD 16 may implement to provide adaptive CRT to patient 14. When it is determined, e.g., by a clinician, that heart 12 of patient 14 is exhibiting intrinsic conduction, e.g., based on an intrinsic conduction time measurement, but one ventricle is contracting out of synchrony with the other, IMD 16 may be configured to generate and deliver fusion pacing therapy to heart 12 of patient 14. In accordance with the technique shown in FIG. 5, processor 80 may control stimulation generator 84 to deliver a fusion pacing pulse to the later contracting ventricle V2, which, in the example described herein, is LV 32 (110). In other examples, the later contracting ventricle V2 may be RV 28.

In the example shown in FIG. 5, after delivering a fusion pacing pulse ($LV_P$) to LV 32, processor 80 determines whether a surrogate indication of intrinsic conduction of RV 28 is detected (112). Example techniques that processor 80 may implement to determine whether the surrogate indication is detected described below with respect to FIGS. 6-11. In some examples, processor 80 may control the delivery of pacing therapy to patient 14 based on the detection of a surrogate indication of intrinsic AV conduction by implementing the technique shown in FIG. 5, or any of the other techniques relating to the surrogate indication described herein (e.g., FIGS. 6-11), if the PEI used to determine a fusion pacing interval is greater than the current blanking interval with which IMD 16 senses electrical cardiac activity of heart 12 following the LV pace event ($LV_P$). Thus, in some examples, prior to implementing the technique shown in any of FIGS. 5-11, processor 80 may determine whether the PEI used to determine the fusion pacing interval with which the fusion pacing pulse is delivered to LV (110) is greater than the current blanking interval.

If the surrogate indication is not detected following the delivery of a fusion pacing pulse (NO branch of block 112), processor 80 may determine there has been a loss of intrinsic AV conduction from RA 26 to RV 28, such that fusion pacing may be less effective for maintaining a desirable cardiac output of heart 12. Accordingly, in response to determining that the surrogate indication of intrinsic AV conduction has not been detected (112), processor 80 may control stimulation generator 84 to switch pacing configurations. In the example shown in FIG. 5, processor 80 controls stimulation generator 84 to terminate fusion pacing and to generate and deliver biventricular pacing to heart 12 (114). For example, processor 80 may control stimulation generator 84 to generate and deliver a first pacing pulse to RV 28 via electrodes of lead 18 and to generate and deliver a second pacing pulse to LV 32 via electrodes of lead 20 in a manner that synchronizes contraction of RV 28 and LV 28.

Processor 80 may also be configured to, in response to detecting the surrogate indication of AV conduction (YES branch of block 112), maintain the fusion pacing configuration. For example, processor 80 may control stimulation generator 84 to generate and deliver another fusion pacing pulse to LV 32 (110). Detection of the surrogate indication of AV conduction may indicate that there has not been a loss of intrinsic AV conduction, such that fusion pacing may still be useful for maintaining a desirable level of cardiac output for patient 14. IMD 16 may continue delivering adaptive CRT to patient 14 using the technique shown in FIG. 5. In the example shown in FIG. 5, after delivering each fusion pacing pulse to LV 32 (110), processor 80 may determine whether the surrogate indication of intrinsic AV conduction is detected (112), such that processor 80 determines whether intrinsic AV conduction is present based on the surrogate indication on a pulse-by-pulse basis.

In other examples, processor 80 may determine whether the surrogate indication of intrinsic RV 28 conduction is detected (112) on a less frequent basis, but more frequently than determining the actual intrinsic conduction time measurement (e.g., by suspending delivery of pacing pulses to LV 32 and RV 28, and determining the time between an atrial pacing or sense event ($A_{P/S}$) and an RV 28 sense event ($RV_S$)). For example, processor 80 may determine whether the surrogate indication of intrinsic RV 28 conduction is detected every other fusion pacing pulse, every three fusion pacing pulses, once a minute, once an hour, or according to another frequency. In some examples, processor 80 may determine the surrogate indication (112) and determine whether the surrogate indication of intrinsic AV conduction indicates a loss of intrinsic AV conduction (114) more than once during a 24 hour period.

Figure 6:
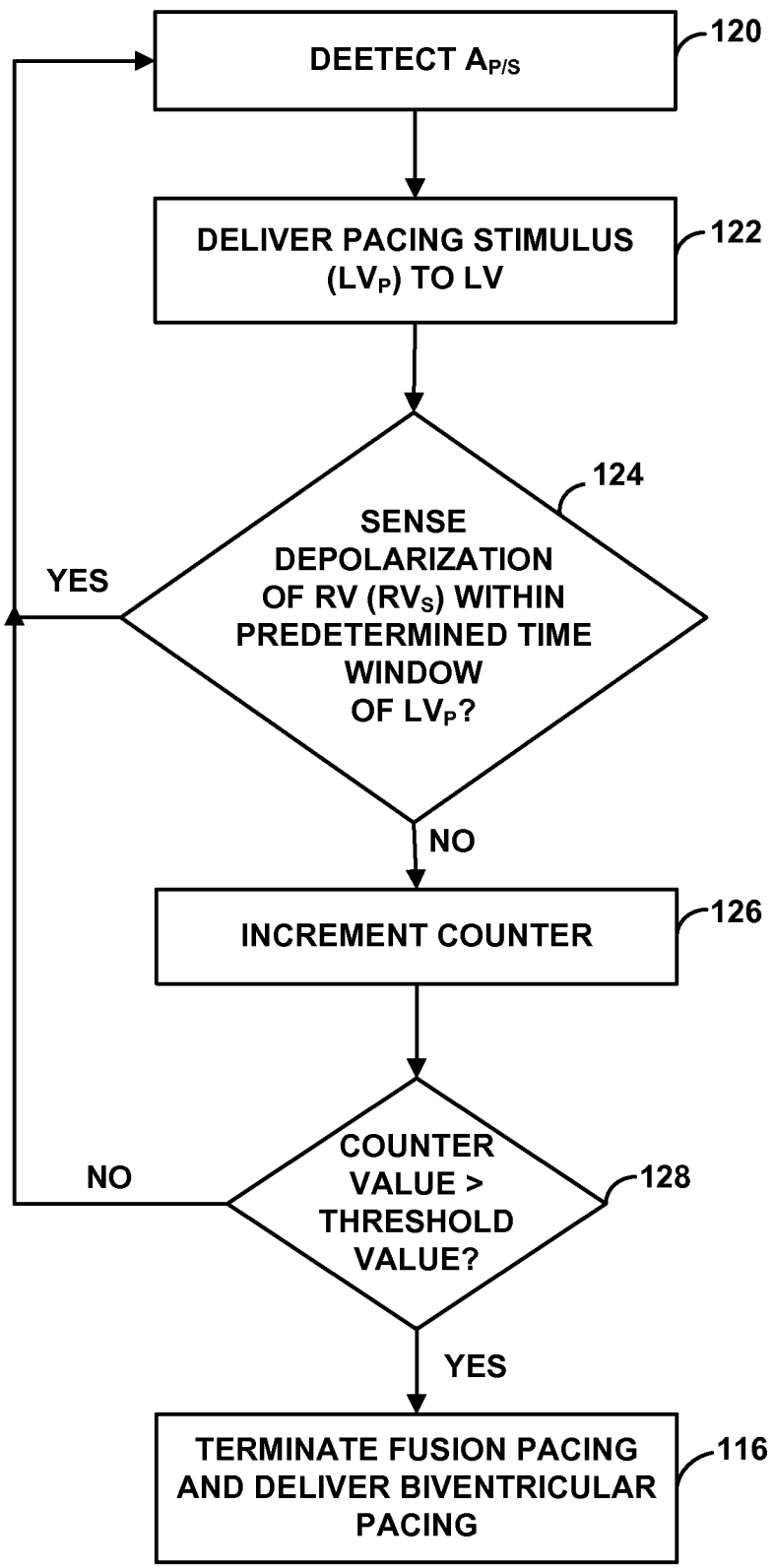

In other examples, rather than immediately switching to biventricular pacing in response to a first failure to detect the surrogate indication of intrinsic AV conduction after the delivery of a fusion pacing pulse to LV 32, processor 80 may determine whether the surrogate indication of intrinsic AV conduction is not detected a certain number of times before switching the pacing configuration of IMD 16 to biventricular pacing. An example of such a technique is shown in FIG. 6, which is a flow diagram of an example technique that IMD 16 may implement to deliver fusion pacing to heart 12 of patient 14. In the example technique shown in FIG. 6, the surrogate indication of intrinsic AV conduction is the detection of a ventricular activation of RV 28 within a predetermined time immediately following the time a pacing stimulus ($LV_P$) to LV 32.

In accordance with the technique shown in FIG. 6, processor 80 (FIG. 3) of IMD 16 controls the delivery of a fusion pacing pulse $LV_P$ to LV 32 (FIG. 2) relative to an atrial pace or sense event ($A_{P/S}$). In particular, in the example shown in FIG. 6, processor 80 detects the atrial pace or sense event ($A_{P/S}$) (120), e.g., by detecting a P-wave in an electrical cardiac signal sensed by sensing module 86 (FIG. 3) or by controlling stimulation generator 84 to generate and deliver a pacing stimulus to RA 26. Thereafter, processor 80 may control stimulation generator 84 of IMD 16 to deliver a pacing stimulus ($LV_P$) to LV 32 (122). For example, after detecting the atrial pace or sense event ($A_{P/S}$), processor 80 may control the delivery of the LV 32 pacing stimulus ($LV_P$) to heart 12 upon expiration of a fusion pacing interval stored by memory 82 of IMD 16 or of another device (e.g., programmer 24). The fusion pacing interval may start at the detection of the atrial pace or sense event ($A_{P/S}$) (120).

After stimulation generator 84 generates and delivers the pacing stimulus ($LV_P$) to LV 32, processor 80 determines whether the surrogate indication of intrinsic AV conduction is detected. In the example shown in FIG. 6, processor 80 controls sensing module 86 to sense electrical cardiac activity and determines whether depolarization of RV 28 ($RV_S$) is detected within a predetermined time window immediately following the time the pacing stimulus ($LV_P$) was delivered to LV 32 (124). In one example, the predetermined time window has a duration of about 30 milliseconds (ms) to about 100 ms and begins immediately following the time the pacing stimulus ($LV_P$) was delivered to LV 32 (e.g., $LV_P$ may be time zero of the predetermine time window). If the blanking interval with which sensing module 86 senses electrical cardiac activity of heart 12 following the LV pace event ($LV_P$) is greater than about the duration of the predetermined time window, processor 80 may shorten the blanking interval in order to detect the surrogate indication of the intrinsic AV conduction.

As discussed in further detail below with reference to FIG. 7, processor 80 may detect the surrogate indication of intrinsic AV conduction by not only determining whether the depolarization of RV 28 ($RV_S$) is detected within a predetermined time window immediately following the time the pacing stimulus ($LV_P$) was delivered to LV 32, but also determining whether the depolarization of RV 28 ($RV_S$) was attributable to the pacing stimulus ($LV_P$) delivered to LV 32. In these examples, processor 80 may characterize the RV sense event ($RV_S$) detected within the predetermined time window immediately following the time the pacing stimulus ($LV_P$) was delivered to LV 32 as the surrogate indication of intrinsic AV conduction if processor 80 also determines that the RV sense event ($RV_S$) was not caused by the pacing stimulus ($LV_P$).

In accordance with the technique shown in FIG. 6, in response to detecting the depolarization of RV 28 ($RV_S$) within the predetermined window of time immediately following the delivery of the pacing stimulus ($LV_P$) to LV 32 (124), processor 80 may determine that the surrogate indication of intrinsic AV conduction was detected, and, therefore, there has not been a loss of intrinsic AV conduction. In response, processor 80 may continue controlling stimulation generator 84 to generate and delivery cardiac rhythm management therapy to heart 12 according to a fusion pacing configuration. As shown in FIG. 6 (YES branch of decision block 124), processor 80 may detect an atrial pace or sense event ($A_{P/S}$) (120) and, thereafter, control stimulation generator 84 to deliver a fusion pacing stimulus ($LV_P$) to LV 32 (122). After stimulation generator 84 delivers the pacing stimulus ($LV_P$) to LV 32, processor 80 determines whether the surrogate indication of intrinsic AV conduction is detected (124).

If, however, processor 80 does not detect the surrogate indication of intrinsic AV conduction after the fusion pacing pulse ($LV_P$) is delivered to LV 32, processor 80 may increment a counter (126). The counter can be implemented by software, hardware, firmware, or any combination thereof. For example, when processor 80 increments the counter, processor 80 may generate a flag, value or other indication generated by processor 80 and stored by memory 82 of IMD 16 or a memory of another device. As another example, the counter may be implemented by a register-type circuit and processor 80 may cause a state of the register-type circuit to change in order to increment or otherwise manage the counter. Counters having other configurations may also be used. In the example shown in FIG. 6, processor 80 determines the surrogate indication of intrinsic AV conduction is not detected in response to determining depolarization of RV 28 ($RV_S$) is not detected within a predetermined time window immediately following the time the pacing stimulus ($LV_P$) was delivered to LV 32 (NO branch of block 124).

In some examples, processor 80 only increments the counter for each consecutive cardiac cycle in which the surrogate indication of intrinsic AV conduction is not detected. In these examples, processor 80 may reset the counter to zero each time the surrogate indication of intrinsic AV conduction is detected. In other examples, processor 80 increments the counter for nonconsecutive cardiac cycle in which the surrogate indication of intrinsic AV conduction is not detected, and resets the counter at other times, e.g., if the surrogate indication is detected for two or more consecutive cardiac cycles.

After processor 80 increments the counter (126), processor 80 may determine whether the value of the counter is greater than a predetermined counter threshold value (128). In some examples, the predetermined counter threshold value is two, while in other examples, the predetermined counter threshold value is one, three, four or more. The predetermined counter threshold value may be value determined by a clinician to be indicative of a loss of intrinsic AV conduction, and may be selected to be low enough to configure IMD 16 to provide a responsive switch in pacing configuration, and to provide responsive cardiac rhythm management therapy. The predetermined counter threshold value may be stored by memory 82 of IMD 16 or a memory of another device with which processor 80 may communicate (e.g., programmer 24).

In some examples, processor 80 restarts the counter each time a surrogate indication of intrinsic AV conduction is detected. In these examples, the counter tracks consecutive, uninterrupted failures to detect the surrogate indication of intrinsic AV conduction. In other examples, processor 80 manages the counter to track the number of failures to detect the surrogate indication of intrinsic AV conduction within a predetermined range of time (e.g., within 30 seconds, one minute or more).

If processor 80 determines that the value of the counter is not greater than the predetermined threshold value (NO branch of block 128), processor 80 may, in response, resume control of fusion pacing to patient 14, e.g., by restarting the technique shown in FIG. 6. For example, processor 80 may detect an atrial pace or sense event ($A_{P/S}$)(120), subsequently control stimulation generator 84 of IMD 16 to deliver a pacing stimulus ($LV_P$) to LV 32 (122), and determine whether the depolarization of RV 28 ($RV_S$) within the predetermined window of time immediately following the delivery of the pacing stimulus ($LV_P$) to LV 32 (124).

If, however, after processor 80 increments the counter (126), processor 80 determines the value of the counter is greater than the predetermined threshold value (Yes branch of block 128), processor 80 may terminate fusion pacing and control stimulation generator 84 to deliver biventricular pacing to heart 12 of patient 14 (116). A value of the counter is greater than the predetermined threshold value may indicate that the intrinsic AV conduction is no longer present or that a change in pacing configuration to better suit the patient's physiological state is desirable.

In other examples of the techniques shown in FIGS. 5 and 6, rather than terminating fusion pacing and controlling stimulation generator 84 to deliver biventricular pacing to heart 12 of patient 14 in response to determining the value of the counter is greater than the predetermined threshold value, processor 80 may control IMD 16 to perform an intrinsic AV conduction time measurement. In one example, processor 80 performs an intrinsic AV conduction time measurement by suspending all cardiac rhythm therapy to RV 28 and LV 32 and determining the time delay between an atrial pace or sense event ($A_{P/S}$) and an RV sense event ($RV_S$) for one or more cardiac cycles. If the measured intrinsic AV conduction times from a plurality of cardiac cycle are used to determine the intrinsic AV conduction time measurement, processor 80 may, for example, determine the intrinsic AV conduction time is the mean or median of the plurality of measured AV conduction times for the cardiac cycles.

In some examples, processor 80 determines the intrinsic conduction time measurement indicates a loss of intrinsic AV conduction if the intrinsic conduction time measurement is greater than (or greater than or equal to) a predetermined threshold value (which differs from the counter threshold discussed above). The predetermined threshold value may be selected to be, for example, a value that indicates the depolarization of RV 28 is delayed to such an extent that cardiac output of heart 12 of patient 14 may not be physiologically sufficient. If the intrinsic conduction time measurement indicates a loss of intrinsic AV conduction, processor 80 may control stimulation generator 84 to terminate fusion pacing and deliver biventricular pacing to heart 12 of patient 14.

As described above, in some examples, sensing module 86 may sense depolarization of RV 28 ($RV_S$) after delivery of a fusion pacing pulse ($LV_P$) to LV 32 even if intrinsic conduction from RA 26 to RV 28 is not actually present. For example, the electrical stimulus delivered to LV 32 may propagate to RV 26 and thereby cause depolarization of RV 26. In these situations, detection of the depolarization of RV 28 that is attributable to the pacing stimulus ($LV_P$) delivered to LV 32 may not be a proper surrogate indication of intrinsic AV conduction. In some examples, as part of the technique for detecting the surrogate indication of intrinsic AV conduction, processor 80 of IMD 16 may determine whether depolarization of RV 28 ($RV_S$) sensed after delivery of a pacing stimulus ($LV_P$) to LV 32 is attributable to the pacing stimulus ($LV_P$).

Figure 7:
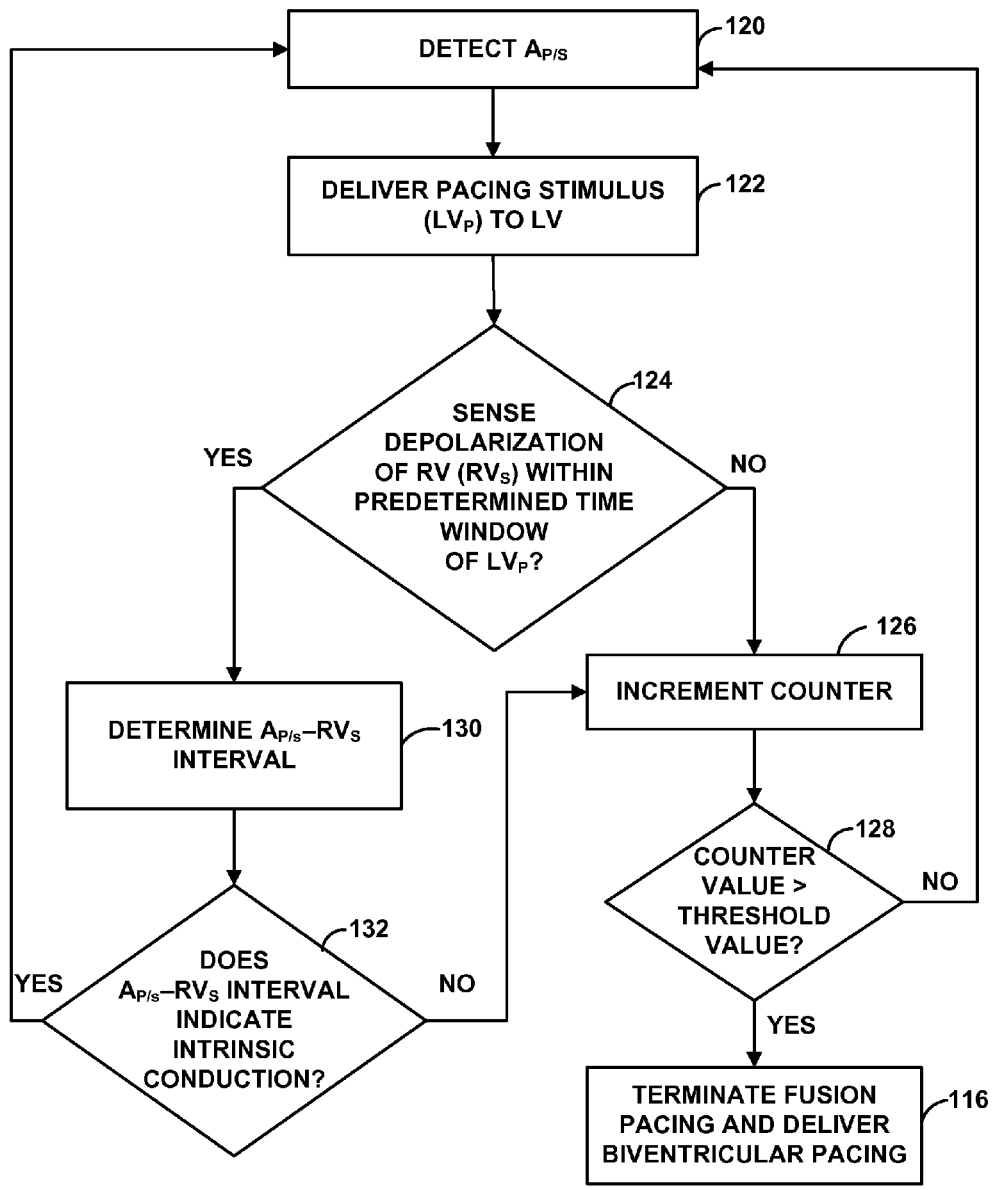
FIGS. 7-9 are flow diagrams of example techniques for determining whether the detection of a sense event in the first depolarizing ventricle of the patient within a predetermined amount of time following the delivery of a fusion pacing stimulus to the later depolarizing ventricle is a surrogate indication of intrinsic AV conduction.

FIG. 7 is a flow diagram of an example technique for determining whether depolarization of RV 28 ($RV_S$) sensed after delivery of a pacing stimulus ($LV_P$) to LV 32 is attributable to the pacing stimulus ($LV_P$) or to intrinsic AV conduction. In the technique shown in FIG. 7, processor 80 controls the stimulation generator 84 to deliver a pacing pulse ($LV_P$) to LV 32 (FIG. 2) at a time that is based on an atrial pace or sense event ($A_{P/S}$). In particular, in the example shown in FIG. 7, processor 80 detects the atrial pace or sense event ($A_{P/S}$) (120), and controls stimulation generator 84 of IMD 16 to deliver a pacing stimulus ($LV_P$) to LV 32 (122) after expiration of a fusion pacing interval that begins at the detection of the atrial pace or sense event ($A_{P/S}$). After stimulation generator 84 generates and delivers the pacing stimulus ($LV_P$) to LV 32, processor 80 determines whether the surrogate indication of intrinsic AV conduction is detected (124). In the example shown in FIG. 7, the surrogate indication is depolarization of RV 28 ($RV_S$) within a predetermined time window immediately following the delivery of the pacing stimulus ($LV_P$) to LV 32.

If processor 80 does not detect the surrogate indication of intrinsic AV conduction (NO branch of block 124 in FIG. 7), processor 80 may increment a counter (126), determine whether the value of the counter is greater than a predetermined threshold value (128), and, if so, terminate fusion pacing and deliver biventricular pacing (116) or take another action, as described with respect to FIG. 6. As also described with respect to FIG. 6, in response to determining the value of the counter is not greater than the predetermined threshold value (NO branch of block 128), processor 80 may control stimulation generator 84 to maintain fusion pacing therapy delivery to LV 32.

In response to detecting the surrogate indication of intrinsic AV conduction (YES branch of block 124 in FIG. 7), processor 80 may determine the $A_{P/S}$–$RV_S$ interval, e.g., by determining the duration of time between the atrial pace or sense event ($A_{P/S}$) and the sensed depolarization of RV 28 ($RV_S$) (130). Thus, the $A_{P/S}$–$RV_S$ interval may indicate the time delay, within a common cardiac cycle, between the atrial activation and the depolarization of RV 28. Processor 80 may then determine whether the $A_{P/S}$–$RV_S$ interval indicates intrinsic AV conduction is present (132). For example, as described below with respect to FIG. 9, processor 80 may determine whether the $A_{P/S}$–$RV_S$ interval is approximately equal (e.g., equal or within a predetermined range) to the most recent intrinsic conduction time measurement, a mean or median of a plurality of the most recent intrinsic conduction time measurements, a greatest intrinsic conduction time measurement of a plurality of the most recent intrinsic conduction time measurements, or a smallest intrinsic conduction time measurement of a plurality of the most recent intrinsic conduction time measurements. In some examples, processor 80 determines whether the $A_{P/S}$–$RV_S$ interval is approximately equal to a selected one of these values, such as equal to or within a predetermined percentage (e.g., about 95% to about 105%, such as about 100%) of the selected value. The recent intrinsic conduction time measurement or a plurality of the most recent intrinsic conduction time measurements can be stored by memory 82 of IMD 16 or a memory of another device, such as programmer 24. In response to determining that $A_{P/S}$–$RV_S$ interval is approximately equal to the selected value that is based on the one or more recent intrinsic conduction time measurements, processor 80 may determine that the $A_{P/S}$–$RV_S$ interval is indicative of the presence of intrinsic conduction of heart 12.

In another example, as described in further detail below with reference to FIG. 8, instead of, or in addition to, determining whether the $A_{P/S}$–$RV_S$ interval is approximately equal to the most recent intrinsic conduction time measurement in order to determine whether the $A_{P/S}$–$RV_S$ interval is indicative of intrinsic AV conduction, processor 80 determines whether the interval of time between the LV 32 pacing stimulus ($LV_P$) and the $RV_S$ sense event detected within the predetermined window of time immediately following the LV pacing stimulus (the interval being referred to as an "$LV_P$–$RV_S$ interval") is less than a duration of time between pacing pulse delivered to LV 32 earlier in time ($LV_{EP}$) following the atrial pacing or sense event ($A_{P/S}$) than the fusion pacing stimulus ($LV_P$) and a subsequent RV 28 sense event ($RV_{S, EP}$). In response to determining the $LV_P$–$RV_S$ interval is less than such a duration of time ($LV_{EP}$–$RV_{S, EP}$), processor 80 may determine that the $A_{P/S}$–$RV_S$ interval is indicative of the presence of intrinsic conduction. In some examples, processor 80 determines that the $A_{P/S}$–$RV_S$ interval is indicative of the presence of intrinsic conduction of heart 12 in response to determining that the $LV_P$–$RV_S$ interval is less such the duration ($LV_{EP}$–$RV_{S, EP}$) and the $A_{P/S}$–$RV_S$ interval is approximately equal to a value that is based on the one or more most recent intrinsic conduction time measurements.

In the technique shown in FIG. 7, in response to determining that the $A_{P/S}$–$RV_S$ interval is not indicative of intrinsic AV conduction (NO branch of block 132), processor 80 determines that the surrogate indication of intrinsic AV conduction is not, in fact, indicative of intrinsic AV conduction and that the depolarization of RV 28 ($RV_S$) sensed within the predetermined window of time immediately following the pacing stimulus delivered to LV 32 ($LV_P$) was attributable to (e.g., caused by) the pacing stimulus delivered to LV 32 ($LV_P$). In response, processor 80 may increment a counter (126), determine whether the value of the counter is greater than a predetermined threshold value (128), and, take the appropriate action based on whether the value of the counter is greater than a predetermined threshold value. For example, processor 80 may terminate fusion pacing and deliver biventricular pacing (116) or perform an intrinsic conduction measurement if the value of the counter is greater than a predetermined threshold value, as described with respect to FIG. 6. In addition, as described with respect to FIG. 6, if the value of the counter is not greater than the predetermined threshold value (NO branch of block 128), processor 80 may resume fusion pacing (120, 122) and, in some examples, restart the technique shown in FIG. 7.

If processor 80 determines that the $A_{P/S}$–$RV_S$ interval is indicative of intrinsic AV conduction (YES branch of block 132), processor 80 determines that RV sense event ($RV_S$) detected within the predetermined window of time following the fusion pacing pulse ($LV_P$) is a surrogate indication of intrinsic AV conduction. In response, processor 80 may control stimulation generator 84 to maintain fusion pacing therapy to heart 12 (120, 122), and, in some examples, restart the technique shown in FIG. 7.

Figure 8:
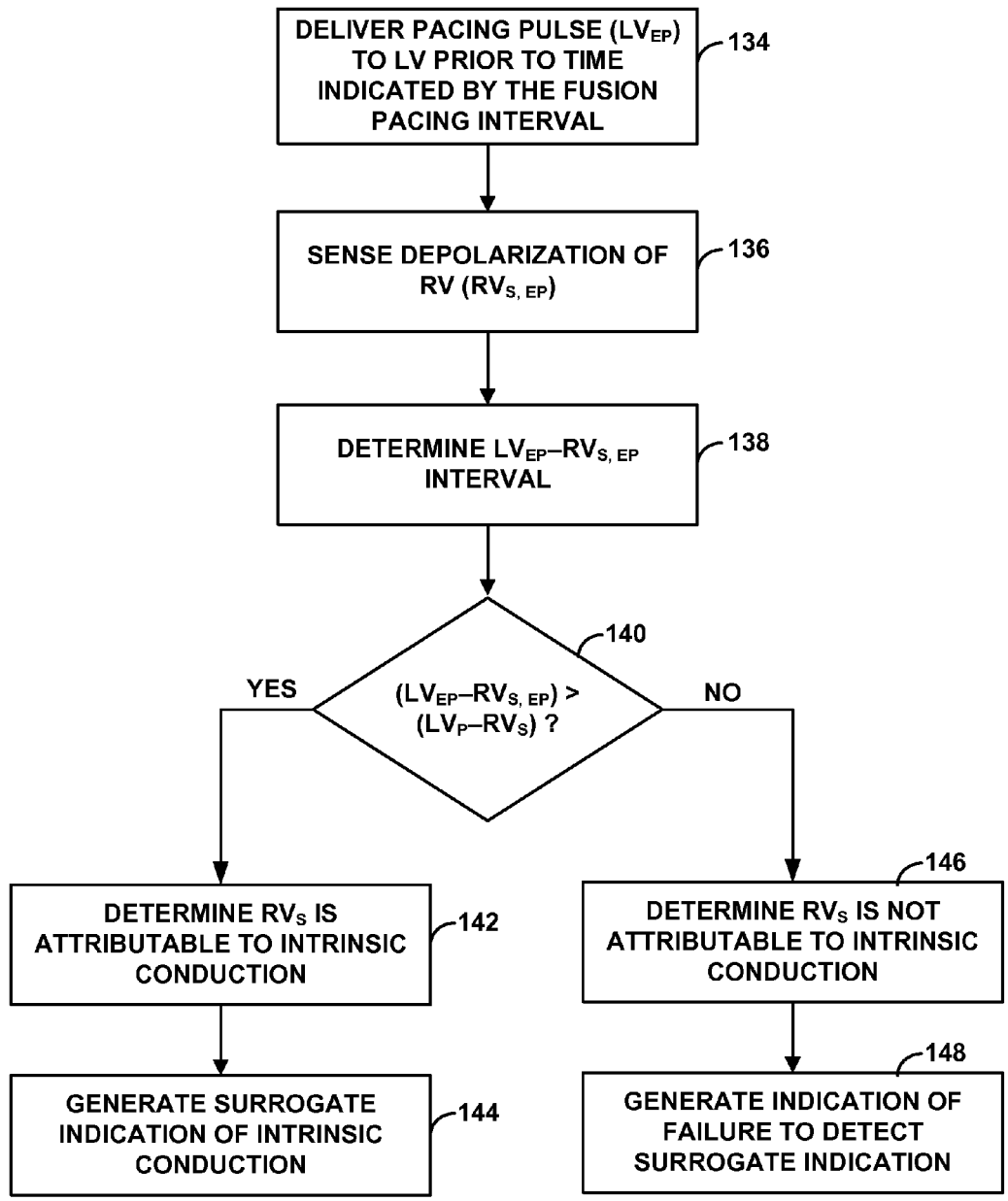

FIG. 8 is a flow diagram of an example technique that may be implemented, e.g., by processor 80, to determine whether an interval of time ($A_{P/S}$–$RV_S$ interval) between an atrial pace or sense event ($A_{P/S}$) and an RV 28 sense event ($RV_S$) sensed within a predetermined window of time immediately following the LV pacing stimulus ($LV_P$) is indicative of intrinsic AV conduction. In some examples, the $A_{P/S}$–$RV_S$ interval may be determined using the technique shown in FIG. 7. In accordance with the technique shown in FIG. 8, processor 80 controls stimulation generator 84 to deliver a pacing pulse to LV 32 ($LV_{EP}$) at a time prior to the time indicated by the fusion pacing interval used to deliver fusion pacing therapy to heart 12 (134). Thus, processor 80 may effectively cause the fusion pacing interval to be temporarily shortened, such that the LV pacing stimulus is delivered closer in time to the atrial pace or sense event of the same cardiac cycle. If the fusion pacing interval is determined using Equation (1), for example, processor 80 may increase the PEI in order to decrease the fusion pacing interval. The pacing interval indicates the time at which stimulation generator 84 delivers the pacing pulse to LV 32 relative to an atrial pace or sense event ($A_{P/S}$). The pacing interval for the early pacing pulse to LV 32 ($LV_{EP}$) is selected to be a duration of time that is short enough to time the earlier pacing pulse to LV 32 ($LV_{EP}$) (relative to an atrial pace or sense event ($A_{P/S}$)) to be before the intrinsic depolarization of RV 28. In some examples, processor 80 sets the pacing interval for the earlier pacing pulse to LV 32 ($LV_{EP}$) to be equal to about zero. In other examples processor 80 sets the pacing interval for the earlier pacing pulse to LV 32 ($LV_{EP}$) by decrementing a stored fusion pacing interval by a predetermined amount, such as about 150 ms.

After stimulation generator 84 delivers the early pacing pulse to LV 32 ($LV_{EP}$), sensing module 84 may sense depolarization of RV 28 ($RV_{S, EP}$) (136) and processor 80 may determine the time delay ($LV_{EP}$–$RV_{S, EP}$) between the early pacing pulse to LV 32 ($LV_{EP}$) and the subsequently detected RV 28 sense event ($RV_{S, EP}$) (138). In some examples, processor 80 determines the $LV_{EP}$–$RV_{S, EP}$ interval (138) less frequently than determining the $A_{P/S}$–$RV_S$ and $LV_P$–$RV_S$ intervals, such as about once a day. For example, processor 80 may control stimulation generator 84 to deliver the early pacing pulse to LV 32 (LV$_{EP}$) only once a day and may store the determined LV$_{EP}$-RV$_{S, EP}$ in memory 82 of IMD 16 or a memory of another device (e.g., a programmer).

According to the technique shown in FIG. 8, processor 80 may determine whether the LV$_{EP}$-RV$_{S, EP}$ interval of the cardiac cycle including the early pacing pulse to LV 32 (LV$_{EP}$) is greater than (or, in some examples, greater than or equal to) the LV$_P$-RV$_S$ interval (determined for a cardiac cycle including the normal fusion pacing interval). Processor may determine the LV$_P$-RV$_S$ interval by, for example, determining (e.g., using the same cardiac cycle for which the A$_{P/S}$-RV$_S$ interval was determined) the interval of time between the LV 32 fusion pacing pulse (LV$_P$) and the RV sense event (RV$_S$) sensed within the predetermined window of time immediately following the LV 32 fusion pacing pulse (LV$_P$). Thus, the LV$_P$-RV$_S$ interval is less than the A$_{P/S}$-RV$_S$ interval. The LV$_P$-RV$_S$ interval may indicate the conduction time without any interference from atrial conduction.

If the LV$_{EP}$-RV$_{S, EP}$ interval is greater than the LV$_P$-RV$_S$ interval (YES branch of block 140), it may indicate that RV 28 sense event (RV$_S$) sensed within the predetermined window of time immediately following the LV 32 pacing pulse (LV$_P$) occurred due to intrinsic AV conduction to RV 28 and not due to propagation of electrical stimulation from the pacing stimulus delivered to LV 32 (LV$_P$) to RV 28. Accordingly, in response determining the LV$_{EP}$-RV$_{S, EP}$ interval is greater than the LV$_P$-RV$_S$ interval (YES branch of block 140), processor 80 may determine that the RV sense event (RV$_S$) is attributable to intrinsic conduction (142). This may also correspond to, for example, the YES branch of block 132 in FIG. 7.

In some examples, processor 80 may generate a surrogate indication of intrinsic conduction (144) in response to determining that the RV sense event (RV$_S$) used to determine the LV$_P$-RV$_S$ interval and the A$_{P/S}$-RV$_S$ interval is attributable to intrinsic conduction (142). The surrogate indication of intrinsic conduction, when generated, indicates that heart 12 of patient 14 is intrinsically conducting, at least from RA 26 to RV 28. As a result, in response to generating the surrogate indication of intrinsic conduction, processor 80 may continue controlling stimulation generator 84 to generate and deliver fusion pacing therapy to heart 12. In some examples, processor 80 generates an indication (144), such as a flag, value, or the like, that corresponds to the surrogate indication of intrinsic conduction, and stores the indication in memory 82 or a memory of another device, such as programmer 24.

In the technique shown in FIG. 8, processor 80 controls stimulation generator 84 to deliver a pacing pulse to LV 32 earlier in time relative to the atrial pace or sense event (A$_{P/S}$) compared to the timing of the fusion pacing pulse delivered to LV 32 that was used to determine the LV$_{EP}$-RV$_{S, EP}$ interval in order to determine whether the pacing stimulus delivered to LV 32 (LV$_P$) is affecting the contraction of RV 28. In some patients, when intrinsic AV conduction is present and all other physiological conditions are equal (e.g., the patient's respiration rate is the same), RV 28 depolarizes at approximately the same time relative to the atrial pace or sense event (A$_{P/S}$), despite the delivery of the pacing stimulus delivered LV 32 (LV$_P$). By shifting the timing of the pacing pulse to LV 32 to be earlier in time relative to the atrial pace or sense event (A$_{P/S}$), processor 80 can determine, based on the timing of the RV sense event (RV$_S$), whether the pacing stimulus is affecting (e.g., evoked) the depolarization of (RV$_S$) by determining whether the RV sense event (RV$_S$) was also earlier in time or occurred at approximately the same time. The RV sense event (RV$_S$) occurring at approximately the same time or at least not earlier in time may be indicated by, for example, the LV$_{EP}$-RV$_{S, EP}$ interval being greater than the LV$_P$-RV$_S$ interval.

In the example shown in FIG. 8, if processor determines that the LV$_{EP}$-RV$_{S, EP}$ interval of the cardiac cycle including the early pacing pulse to LV 32 (LV$_{EP}$) is not greater than the LV$_P$-RV$_S$ interval (NO branch of block 140), processor 80 may determine that the depolarization of RV 28 indicated by the RV sense event (RV$_S$) was at least partially attributable to the pacing stimulus delivered to LV 32 (LV$_P$) (146). Processor 80 may, accordingly, determine that no surrogate indication of intrinsic AV conduction was detected based on the RV sense event (RV$_S$). In response to determining that the LV$_{EP}$-RV$_{S, EP}$ is not greater than the LV$_P$-RV$_S$ interval, processor 80 may generate an indication of a failure to detect the surrogate indication of intrinsic AV conduction (148). In some examples, processor 80 generates the indication of the failure to detect the surrogate indication (148) by at least generating a flag, value, or the like that corresponds to the indication of the failure to detect the surrogate indication, and storing the indication in memory 82 or a memory of another device, such as programmer 24.

The generation of the indication of a failure to detect the surrogate indication of intrinsic AV conduction (148) may correspond to the NO branch of block 132 in FIG. 7. As shown in FIG. 7, in response to determining there is no indication of intrinsic AV conduction, processor 80 may increment a counter (126), determine whether the counter value is greater than a predetermined threshold value (128), and take an appropriate action based on the determination (116, 120).

As discussed above, in some examples, processor 80 of IMD 16 may confirm that the RV 28 sense event (RV$_S$) detected within a predetermined window of time following the delivery of a fusion pacing pulse (LV$_P$) is indicative of intrinsic AV conduction based on a comparison of the time interval between the atrial pace or sense event (A$_{P/S}$) and the RV 28 sense event (RV$_S$) (A$_{P/S}$-RV$_S$) to an intrinsic conduction time measurement. The RV 28 sense event (RV$_S$) used (e.g., by processor 80) to determine the A$_{P/S}$-RV$_S$ interval is the same as the RV 28 sense event used (e.g., by processor 80) to determine the LV$_P$-RV$_S$ discussed with respect to FIG. 8.

Figure 9:
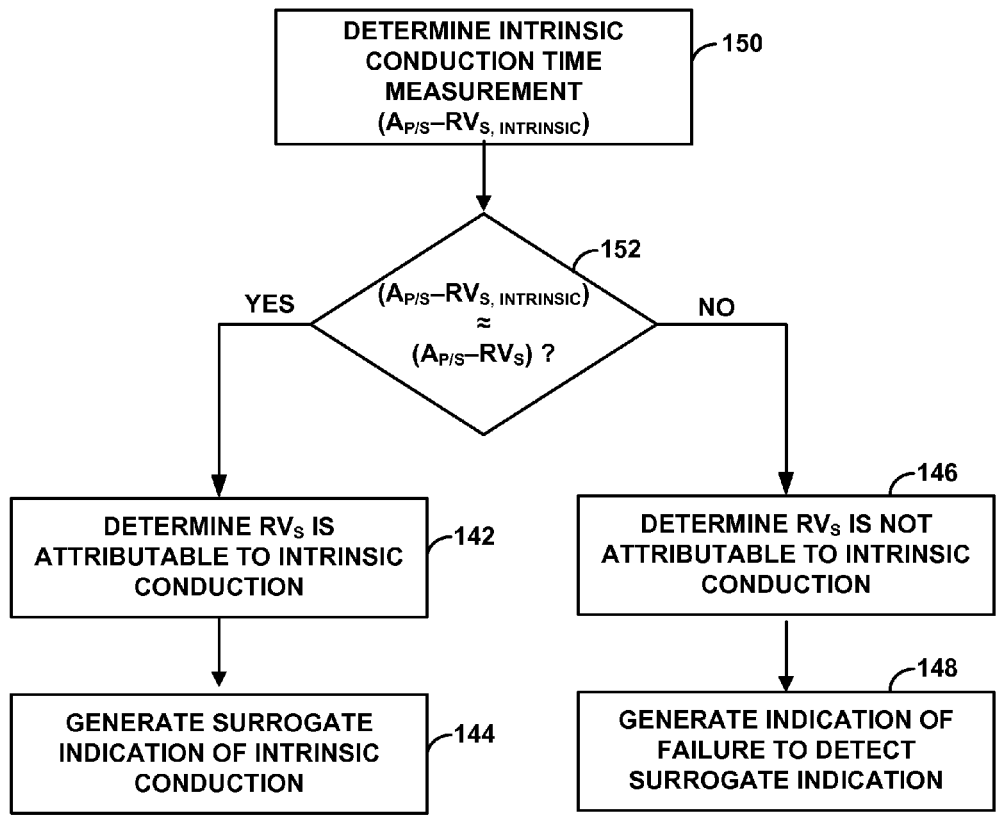

FIG. 9 is a flow diagram of an example technique that may be implemented to determine, based on such a comparison between the A$_{P/S}$-RV$_S$ interval and one or more intrinsic conduction time measurements, whether the RV 28 sense event (RV$_S$) was attributable to intrinsic AV conduction.

In accordance with the technique shown in FIG. 9, processor 80 may determine an intrinsic conduction time measurement (A$_{P/S}$-RV$_{S, INTRINSIC}$) (150). The intrinsic conduction time measurement may be, for example, part of a capture management test measurement performed by processor 80. In some examples, processor 80 determines the intrinsic conduction time measurement by suspending at least the pacing therapy delivered to RV 28 and LV 32 to allow the heart of the patient to conduct in the absence of cardiac rhythm management therapy. In some examples, however, pacing to RA 26 or LA 33 may be maintained. Processor 80 may then detect, based on electrical cardiac activity sensed by sensing module 86, a RV 28 sense event (RV$_S$), and, in some cases, an RA sense event. Processor 80 may determine the measurement of intrinsic conduction time to be the time between an atrial pace or sense event (A$_{P/S}$) and the RV sensing event (RV$_S$). In some examples, processor 80 stores the intrinsic conduction time measurement in memory 82 of IMD 16 or a memory of another device.

After processor 80 determines the intrinsic conduction time measurement (A$_{P/S}$-RV$_{S, INTRINSIC}$) (150), processor 80 may determine whether the $A_{P/S}$–$RV_S$ interval is approximately equal to the intrinsic conduction time measurement ($A_{P/S}$–$RV_{S, INTRINSIC}$) (152). For example, processor 80 may determine whether the $A_{P/S}$–$RV_S$ interval is within a predetermined range of the intrinsic conduction time measurement ($A_{P/S}$–$RV_{S, INTRINSIC}$), such as equal to or within a predetermined percentage (e.g., about 5% to about 15%, such as about 10%) of the intrinsic conduction time measurement ($A_{P/S}$–$RV_{S, INTRINSIC}$). In other examples, processor 80 may determine whether the $A_{P/S}$–$RV_S$ interval is approximately equal to a mean or median of a plurality of the most recent intrinsic conduction time measurements, a greatest intrinsic conduction time measurement of a plurality of the most recent intrinsic conduction time measurements, or a smallest intrinsic conduction time measurement of a plurality of the most recent intrinsic conduction time measurements.

In response to determining the $A_{P/S}$–$RV_S$ interval is approximately equal to the intrinsic conduction time measurement ($A_{P/S}$–$RV_{S, INTRINSIC}$) (YES branch of block 152), processor 80 may determine that the RV sense event ($RV_S$) used to determine the $A_{P/S}$–$RV_S$ interval is indicative of the presence of intrinsic conduction of heart 12 (142) and may generate a surrogate indication of intrinsic conduction (144), as described above with respect to FIG. 8.

On the other hand, in response to determining that the $A_{P/S}$–$RV_S$ interval is not approximately equal to the intrinsic conduction time measurement ($A_{P/S}$–$RV_{S, INTRINSIC}$) (NO branch of block 152), processor 80 may determine that the RV sense event ($RV_S$) used to determine the $A_{P/S}$–$RV_S$ interval is not indicative of the presence of intrinsic conduction of heart 12 (146) and may generate an indication of a failure to detect the surrogate indication (148), as described above with respect to FIG. 8.

Figure 10:
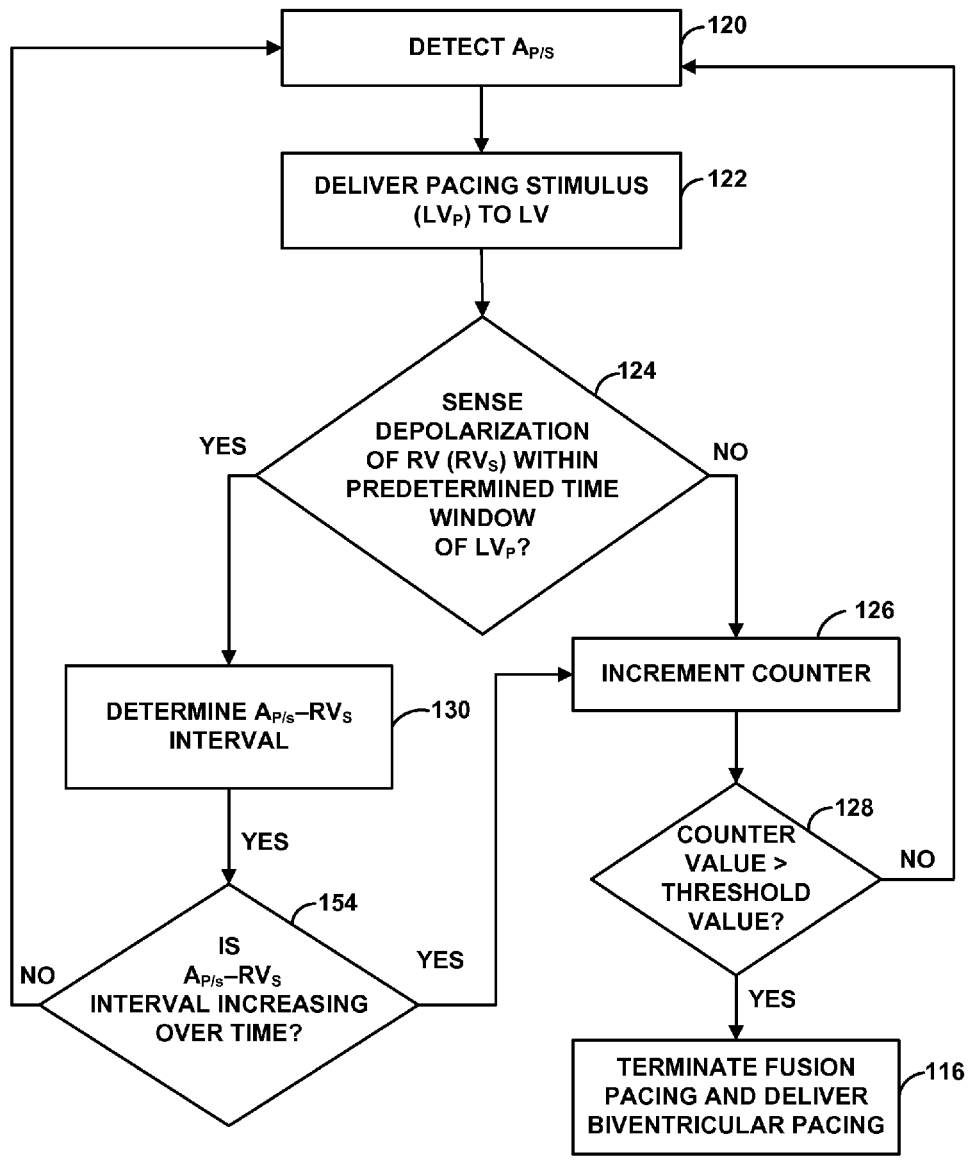
FIG. 10 is a flow diagram of an example technique for determining whether a pattern in $A_{P/S}$–$V1_S$ intervals over time is indicative of loss of intrinsic AV conduction.

FIG. 10 is a flow diagram of an example technique that may be implemented to determine whether a pattern of determined $A_{P/S}$–$RV_S$ intervals over time may indicate a loss of intrinsic AV conduction. Processor 80 may implement the technique shown in FIG. 10 to, for example, determine whether the $A_{P/S}$–$RV_S$ intervals indicate a change in pacing configuration from a fusion pacing configuration to a biventricular pacing configuration is desirable, or to determine whether to perform an intrinsic conduction time measurement to confirm the presence of intrinsic AV conduction.

As shown in FIG. 10, processor 80 may detect an atrial pace or sense event ($A_{P/S}$) (120) and, thereafter, control stimulation generator 84 to deliver a fusion pacing stimulus ($LV_P$) to LV 32, e.g., using a fusion pacing interval that is timed relative to the atrial pace or sense event ($A_{P/S}$) (122). After stimulation generator 84 delivers the pacing stimulus ($LV_P$) to LV 32, processor 80 may determine whether sensing module 86 sensed depolarization of RV 28 ($RV_S$) within a predetermined time window immediately following the time the pacing stimulus ($LV_P$) was delivered to LV 32 (124).

As discussed with respect to FIG. 7, in response to determining that the depolarization of RV 28 ($RV_S$) was not sensed within a predetermined time window immediately following the delivery of the pacing stimulus ($LV_P$) (NO branch of block 124), processor 80 may determine that the surrogate indication of intrinsic AV conduction was not detected. In response, processor 80 may increment a counter (126), and determine whether the counter value is greater than (or, in some examples, greater than or equal to) a threshold value (128). If the counter value is greater than the threshold value (YES branch of block 128), processor 80 may switch from a fusion pacing configuration to a biventricular pacing configuration (116), as shown in FIG. 10, or may suspend fusion pacing and perform an intrinsic AV conduction time measurement. If the counter value is not greater than the threshold value (NO branch of block 128), processor 80 may resume fusion pacing (120, 122), as shown in FIG. 10.

In response to determining the depolarization of RV 28 ($RV_S$) was sensed within a predetermined time window immediately following the delivery of the pacing stimulus ($LV_P$) (YES branch of block 124), processor 80 may determine the $A_{P/S}$–$RV_S$ interval (130). In the technique shown in FIG. 10, processor 80 determines whether THE $A_{P/S}$–$RV_S$ interval is increasing over time (154). In some examples, processor 80 makes this determination based on the plurality of $A_{P/S}$–$RV_S$ intervals (of respective cardiac cycles) determined within a particular time frame (e.g., the past 30-60 minutes or a specified number of most recent $A_{P/S}$–$RV_S$ interval determinations, such as the 10-50 most recent $A_{P/S}$–$RV_S$ intervals).

Processor 80 may determine the $A_{P/S}$–$RV_S$ interval is increasing over time (154) using any suitable technique. In one example, processor 80 determines the $A_{P/S}$–$RV_S$ interval is increasing over time if a certain number of consecutive $A_{P/S}$–$RV_S$ intervals (e.g., one, two, three, or more) have increased relative to the prior $A_{P/S}$–$RV_S$ interval determinations, e.g., by a threshold amount (e.g., 1 ms to about 5 ms). As another example, processor 80 may determine the $A_{P/S}$–$RV_S$ interval is increasing over time if the average of the $A_{P/S}$–$RV_S$ intervals for a particular time frame has increased, e.g., by a threshold amount (e.g., 1 ms to about 5 ms), relative to the average of $A_{P/S}$–$RV_S$ interval for the immediate prior time frame. In another example, processor 80 may determine the $A_{P/S}$–$RV_S$ interval is increasing over time if the difference between the $A_{P/S}$–$RV_S$ interval of the most recent cardiac cycle (or a short-term average) and a longer-term average is greater than or equal to a predetermined number, which may be the cumulative sum of the differences or a fixed value. Other techniques may be used to determine whether the $A_{P/S}$–$RV_S$ interval is increasing over time.

In response to determining the $A_{P/S}$–$RV_S$ interval (for respective cardiac cycles) is increasing over time (YES branch of block 154), processor 80 may determine that there may be a loss of intrinsic AV conduction, such that the RV 28 sense event ($RV_S$) is not indicative of intrinsic AV conduction. Thus, in response to determining that the $A_{P/S}$–$RV_S$ interval is increasing over time (YES branch of block 154), processor 80 may increment a counter (126), and determine whether the counter value is greater than (or, in some examples, greater than or equal to) a threshold value (128). Processor 80 may take the appropriate action upon determining whether the counter value is greater than the threshold value (116, 120).

In response to determining that the $A_{P/S}$–$RV_S$ interval is not increasing over time (NO branch of block 154), processor 80 may determine that the right ventricular sense event (RVs) is indicative of intrinsic AV conduction, such that the surrogate indication of intrinsic AV conduction is detected. Processor 80 may then maintain the fusion pacing configuration (120, 122), as shown in FIG. 10.

Other techniques in addition to, or instead of, the techniques described with respect to FIGS. 7-10 may be used to determine whether an RV sense event ($RV_S$) detected within a predetermined time window immediately following the time the pacing stimulus ($LV_P$) was delivered to LV 32 was attributable to intrinsic conduction or to paced activation from the LV 32 pacing stimulus ($LV_P$), and, therefore, whether the RV sense event ($RV_S$) may be a surrogate indication of the presence of intrinsic conduction of heart 12. In some examples, processor 80 determines whether the RV sense event ($RV_S$) detected within a predetermined time window following the time the pacing stimulus ($LV_P$) was delivered to LV 32 was attributable to intrinsic conduction based on an amplitude of the electrical cardiac signal used to detect the RV sense event. The amplitude of the electrical cardiac signal sensed within the predetermined time window immediately following the time the pacing stimulus ($LV_P$) was delivered to LV 32 may differ depending on whether RV 28 depolarized due to a paced activation from the LV 32 pacing stimulus ($LV_P$) or due to intrinsic AV conduction. While the amplitude of the R-wave of an EGM is primarily referred to herein, in other examples, other waves of an EGM or other electrical cardiac signals may be used to determine whether the RV sense event ($RV_S$) was attributable to intrinsic conduction.

Figure 11:
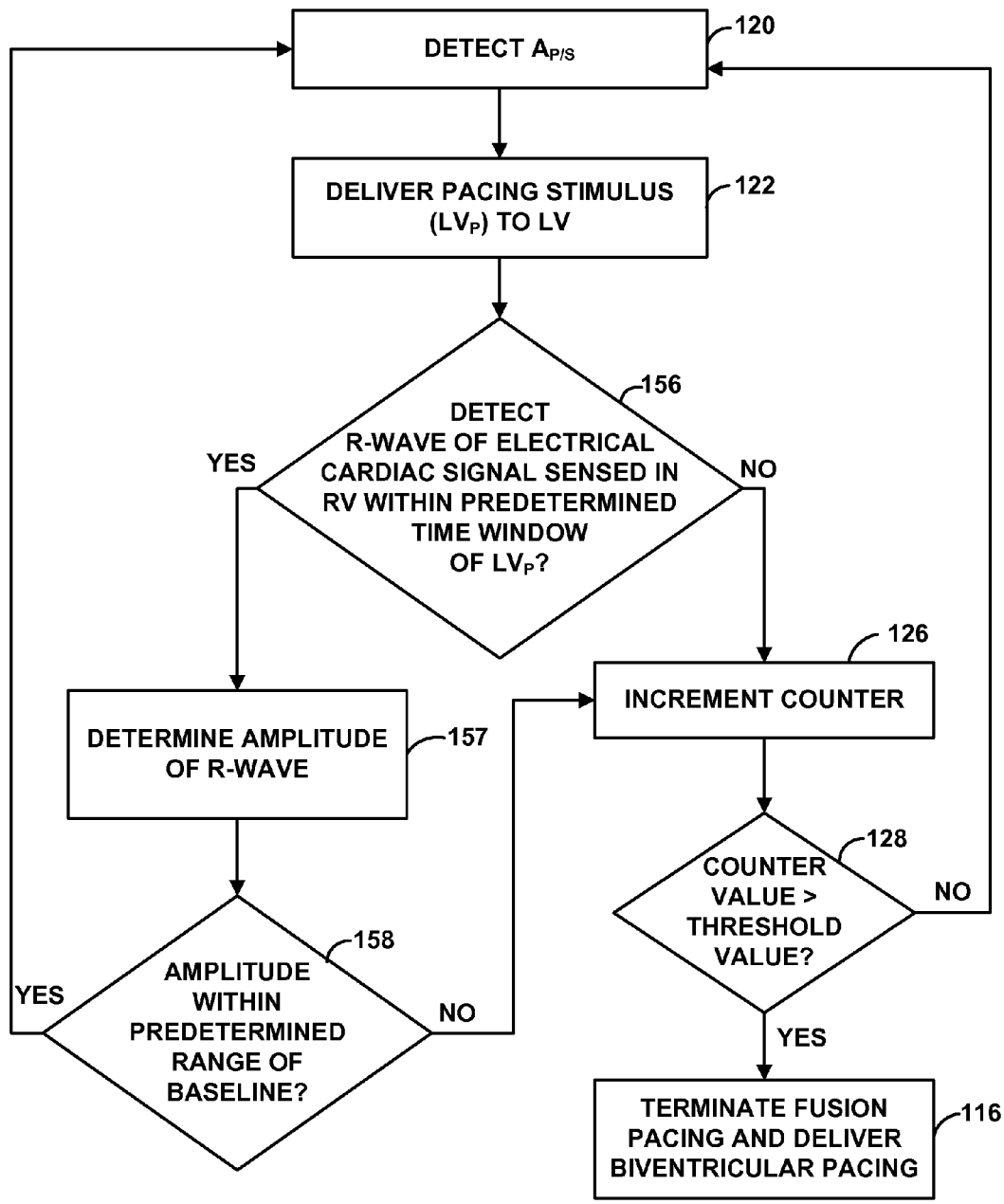
FIG. 11 is a flow diagram of another example technique for determining the detection of a sense event in the first depolarizing ventricle of the patient within a predetermined amount of time following the delivery of a fusion pacing stimulus to the later depolarizing ventricle is a surrogate indication of intrinsic AV conduction.

FIG. 11 is a flow diagram of another example technique for determining whether depolarization of RV 28 ($RV_S$) sensed after delivery of a pacing stimulus ($LV_P$) to LV 32 is attributable to the pacing stimulus ($LV_P$). In accordance with the technique shown in FIG. 11, processor 80 detects an atrial pace or sense event ($A_{P/S}$) (120), and controls stimulation generator 84 of IMD 16 to deliver a pacing stimulus ($LV_P$) to LV 32 (122) after expiration of a fusion pacing interval that begins at the detection of the atrial pace or sense event ($A_{P/S}$). After stimulation generator 84 generates and delivers the pacing stimulus ($LV_P$) to LV 32, processor 80 determines whether an R-wave of an EGM (indicating activity of heart 12) is detected within a predetermined time window immediately following the delivery of the pacing stimulus ($LV_P$) to LV 32 (156). The detection of the R-wave may indicate depolarization of RV 28 ($RV_S$).

If processor 80 does not detect the R-wave of the EGM within the predetermined window of time (NO branch of block 156 in FIG. 11), processor 80 may increment a counter (126), determine whether the value of the counter is greater than a predetermined threshold value (128), and, if so, terminate fusion pacing and deliver biventricular pacing (116) or take another action, as described with respect to FIG. 6. As also described with respect to FIG. 6, in response to determining the value of the counter is not greater than the predetermined threshold value (NO branch of block 128), processor 80 may control stimulation generator 84 to maintain fusion pacing therapy delivery to LV 32.

In the technique shown in FIG. 11, in response to detecting the R-wave within the predetermined window of time (YES branch of block 156 in FIG. 7), processor 80 determines the amplitude of the R-wave (157). Processor 80 may then determine whether the amplitude of the R-wave is within a predetermined range of a baseline amplitude value (158). The amplitude of the R-wave of an electrical cardiac signal sensed within RV 28 may differ depending on whether RV 28 depolarized due to a paced activation from the LV 32 pacing stimulus ($LV_P$) or due to intrinsic AV conduction.

Figures 12, 13:
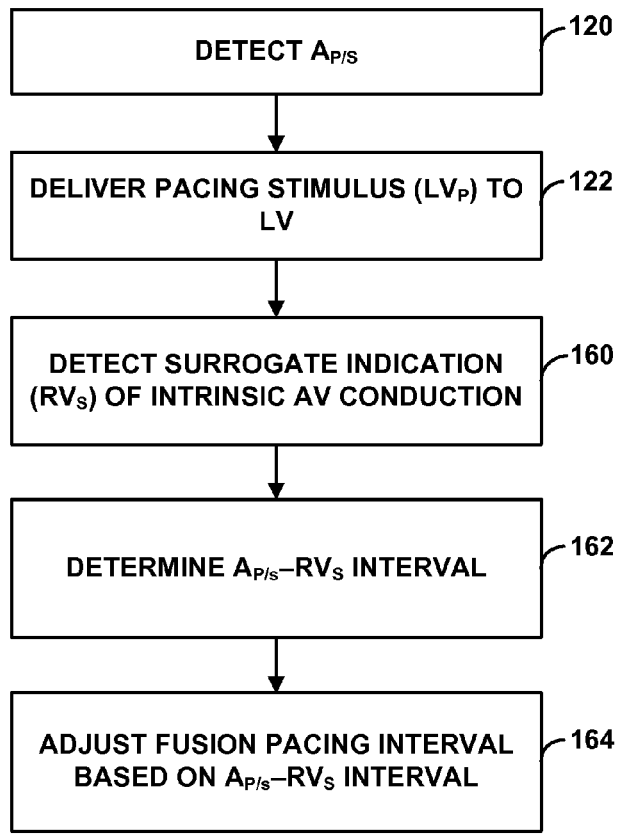
FIG. 12 is a table that compares example a peak R-wave amplitude of a cardiac electrogram when the R-wave is known to be attributable to a pacing pulse to a peak R-wave amplitude of a cardiac electrogram when the R-wave is known to be attributable to intrinsic conduction.
FIG. 13 is a flow diagram of an example technique that may be implemented to adjust a fusion pacing interval based on one or more $A_{P/S}$–$V1_S$ intervals.

FIG. 12 is a table that includes data that indicates the amplitude of an R-wave may change depending on whether the R-wave was caused by intrinsic AV conduction or by an LV pacing pulse. FIG. 12 illustrates, for 24 human subjects, the peak R-wave amplitude of an EGM when the R-wave is known to be attributable to a pacing pulse (labeled in FIG. 12 as "LV-RV Conduction Peak R-Wave EGM amplitude"). These R-wave amplitude values were determined based on an EGM sensed during an LV capture management test. FIG. 12 also illustrates, for the same 24 human subjects, the peak R-wave amplitude of an EGM when the RV depolarized due to intrinsic conduction (referred to in FIG. 12 as "AV Conduction Peak R-Wave EGM amplitude"). These R-wave amplitude values were determined based on an EGM sensed during an intrinsic conduction time measurement determination. The values indicated a "BLOCK" indicate that AV-block was detected.

As shown in FIG. 12, the "LV-RV Conduction Peak R-Wave EGM amplitude" value for each subject differs from the "AV Conduction Peak R-Wave EGM amplitude" value, such that the amplitude value of an R-wave may indicate whether RV depolarized due to intrinsic AV conduction or due to paced activation.

Returning now to FIG. 11, the baseline amplitude value may be, for example, a predetermined amplitude value for an R-wave that indicates RV 28 depolarized due to intrinsic AV conduction. In some examples, the baseline amplitude value is predetermined, e.g., by a clinician, and stored by memory 82 of IMD 16 or a memory of another device (e.g., programmer 24). In other examples, processor 80 automatically determines the baseline amplitude value, e.g., based on the electrical cardiac signal sensed in RV 28 as part of an intrinsic conduction time measurement determination (e.g., when no pacing is delivered to LV 32) or based on an electrical cardiac signal otherwise known to be sensed when intrinsic AV conduction is present in heart 12.

The predetermined range of the baseline amplitude value may also be stored by memory 82 of IMD 16 or a memory of another device (e.g., programmer 24). The predetermined range of the baseline amplitude value may indicate, for example, the variance of the R-wave amplitude value relative to the baseline amplitude value that indicates the R-wave is attributable to intrinsic AV conduction. In some examples, the predetermined range may be, for example, within about 2 millivolts (mV) (e.g., 2 mV or nearly 2 mV) of the baseline amplitude value. In other examples, the predetermined range may be a percentage of the baseline amplitude value, such as within about 5% of the baseline amplitude value. Other predetermined ranges may be used.

In response to determining the amplitude of the R-wave is within the predetermined range of the baseline amplitude value (YES branch of block 158), processor 80 may determine that the RV sense event ($RV_S$) is indicative of intrinsic AV conduction. In the example shown in FIG. 11, in response to determining the amplitude of the R-wave is within the predetermined range of the baseline amplitude value, processor controls stimulation generator 84 to deliver a fusion pacing stimulus to heart 12 for the next cardiac cycle (120, 122). Processor 80 may, in some examples, repeat the technique shown in FIG. 11 for the next cardiac cycle.

On the other hand, in response to determining the amplitude of the R-wave is within the predetermined range of the baseline amplitude value, processor 80 may determine that the RV sense event ($RV_S$) is not a surrogate indication of intrinsic AV conduction (NO branch of block 158), and may increment counter (126), determine whether the value of the counter is greater than a predetermined threshold value (128), and so forth.

The technique shown in FIGS. 7-11 can also be used in combination with each other in some examples. For example, if any one or more of the comparison of a determined $A_{P/S}$–$RV_S$ interval to a predetermined measurement of intrinsic conduction time (e.g., as described with respect to FIG. 7 and FIG. 9), a comparison of the $LV_P$–$RV_S$ interval to a time delay between an early pacing pulse to LV 32 ($LV_{EP}$) and a subsequent RV 28 sense event ($RV_{S, EP}$) (e.g., as described with respect to FIG. 8), a pattern of determined $A_{P/S}$–$RV_S$ intervals over time (as described with respect to FIG. 10), an amplitude of an R-wave sensed within the predetermined window of time, indicates the RV sense event ($RV_S$) detected within a predetermined window of time after the delivery of a fusion pacing stimulus to LV 32 ($LV_P$) is not attributable to intrinsic AV conduction or otherwise indicates a loss of intrinsic AV conduction, processor 80 may take a responsive action. Example responsive actions include, for example, determining an intrinsic A-RV conduction time measurement by suspending all stimulation delivery to heart 12 or suspending delivery of fusion pacing to heart 12 and initiating delivery of biventricular pacing to heart 12.

FIG. 13 is a flow diagram of an example technique that may be implemented to adjust a fusion pacing interval based on an $A_{P/S}$-$RV_S$ interval determined using the RV sense event (RVs) detected within a predetermined window of time after the delivery of a fusion pacing stimulus to LV 32 ($LV_P$). In the technique shown in FIG. 13, processor 80 controls stimulation generator 84 to generate and deliver fusion pacing therapy to heart 12 of patient 14. For example, processor 80 may detect an atrial pace or sense event ($A_{P/S}$) (120) and, thereafter, control stimulation generator 84 to deliver a fusion pacing stimulus ($LV_P$) to LV 32 (122), e.g., at a time determined based on a fusion pacing interval. In the technique shown in FIG. 13, processor 80 detects the surrogate indication of intrinsic AV conduction (160), e.g., using the techniques shown in FIGS. 6-11 and discussed above. Processor 80 may, for example, detect a RV 28 sense event ($RV_S$) within a predetermined window of time following the delivery of the fusion pacing pulse ($LV_P$) and use the techniques described with respect to FIGS. 6-11 to determine that the activation of RV 28 indicated by the RV sense event was not caused by the delivery of the fusion pacing pulse to LV 32.

Processor 80 determines the $A_{P/S}$-$RV_S$ interval after detecting the surrogate indication of intrinsic AV conduction (162). In the example technique shown in FIG. 13, processor 80 may also determine the $A_{P/S}$-$RV_S$ interval is attributable to intrinsic conduction, e.g., using the techniques described with respect to FIGS. 8-11. After determining the $A_{P/S}$-$RV_S$ interval, processor 80 may adjust a fusion pacing interval ($A_{P/S}$-$LV_P$) based on the $A_{P/S}$-$RV_S$ interval (164). As discussed above, in some examples, processor 80 determines a fusion pacing interval based on an intrinsic AV conduction time measurement. In accordance with the technique shown in FIG. 13, processor 80 may adjust the fusion pacing interval by using the $A_{P/S}$-$RV_S$ interval instead of the intrinsic AV conduction time measurement. The $A_{P/S}$-$RV_S$ interval may be, for example, a single $A_{P/S}$-$RV_S$ interval or a mean, median, greatest, or smallest $A_{P/S}$-$RV_S$ interval of a plurality of $A_{P/S}$-$RV_S$ intervals determined by processor 80 within a predetermined time frame. In some examples, processor 80 determines the fusion pacing interval based on the $A_{P/S}$-$RV_S$ interval instead of the intrinsic AV conduction time measurement at all times. In other examples, processor 80 only periodically adjusts the fusion pacing interval based on the $A_{P/S}$-$RV_S$ interval instead of the intrinsic AV conduction time measurement.

In one example, processor 80 may determine an adjusted fusion pacing interval ($A_{P/S}$-$LV_P$) based on the $A_{P/S}$-$RV_S$ interval by decrementing the $A_{P/S}$-$RV_S$ interval by a PEI, as show in Equation (5) below:

$$A_{P/S}\text{-}LV_P = (A_{P/S}\text{-}RV_S) - \text{PEI} \qquad \text{Equation (5)}$$

The PEI shown in Equation (5) may be any suitable PEI, such as the ones described above with respect to Equation (1). T As discussed above, in some examples, processor 80 determines a fusion pacing interval using Equation (1), whereby processor 80 decrements an intrinsic AV conduction time measurement ($A_{P/S}$-$RV_{S,\ INTRINSIC}$) by a PEI in order to determine the fusion pacing interval. In these examples, processor 80 may periodically adjust the fusion pacing interval using Equation (5).

In some examples in which the intrinsic AV conduction time measurement ($A_{P/S}$-$RV_{S,\ INTRINSIC}$) is used to determine (e.g., initially determine or adjust) the fusion pacing interval, the intrinsic AV conduction time measurement ($A_{P/S}$-$RV_{S,\ INTRINSIC}$) is determined less frequently than the $A_{P/S}$-$RV_S$ interval. For example, processor 80 may only determine the intrinsic AV conduction time ($A_{P/S}$-$RV_{S,\ INTRINSIC}$) once every 24 hours, and may determine the $A_{P/S}$-$RV_S$ interval once every cardiac cycle (every heart beat). Thus, processor 80 may be configured to update the fusion pacing interval based on the $A_{P/S}$-$RV_S$ interval more frequently than based on the intrinsic AV conduction time measurement. In some examples, processor 80 is configured to adjust the fusion pacing interval on a beat-to-beat basis based on the $A_{P/S}$-$RV_S$ interval determined for the prior cardiac cycle.

In examples in which processor determines the $A_{P/S}$-$RV_S$ interval more frequently than the actual intrinsic conduction time measurement, and processor 80 adjusts a fusion pacing interval based on the $A_{P/S}$-$RV_S$ interval, processor 80 may provide an adjustment to the fusion pacing interval that is more responsive to the cardiac status (e.g., the cardiac output needs) of patient 14 compared to examples in which processor 80 adjusts a fusion pacing interval based on actual intrinsic conduction time measurements alone. In addition, or instead, in some examples in which processor 80 is configured to adjust a fusion pacing interval based on the $A_{P/S}$-$RV_S$ interval, processor 80 may determine the intrinsic AV conduction time measurement less frequently, such that the suspension of the delivery of pacing stimuli to heart 12 that may occur during the intrinsic AV conduction time measurement may occur less frequently.

Figure 14:
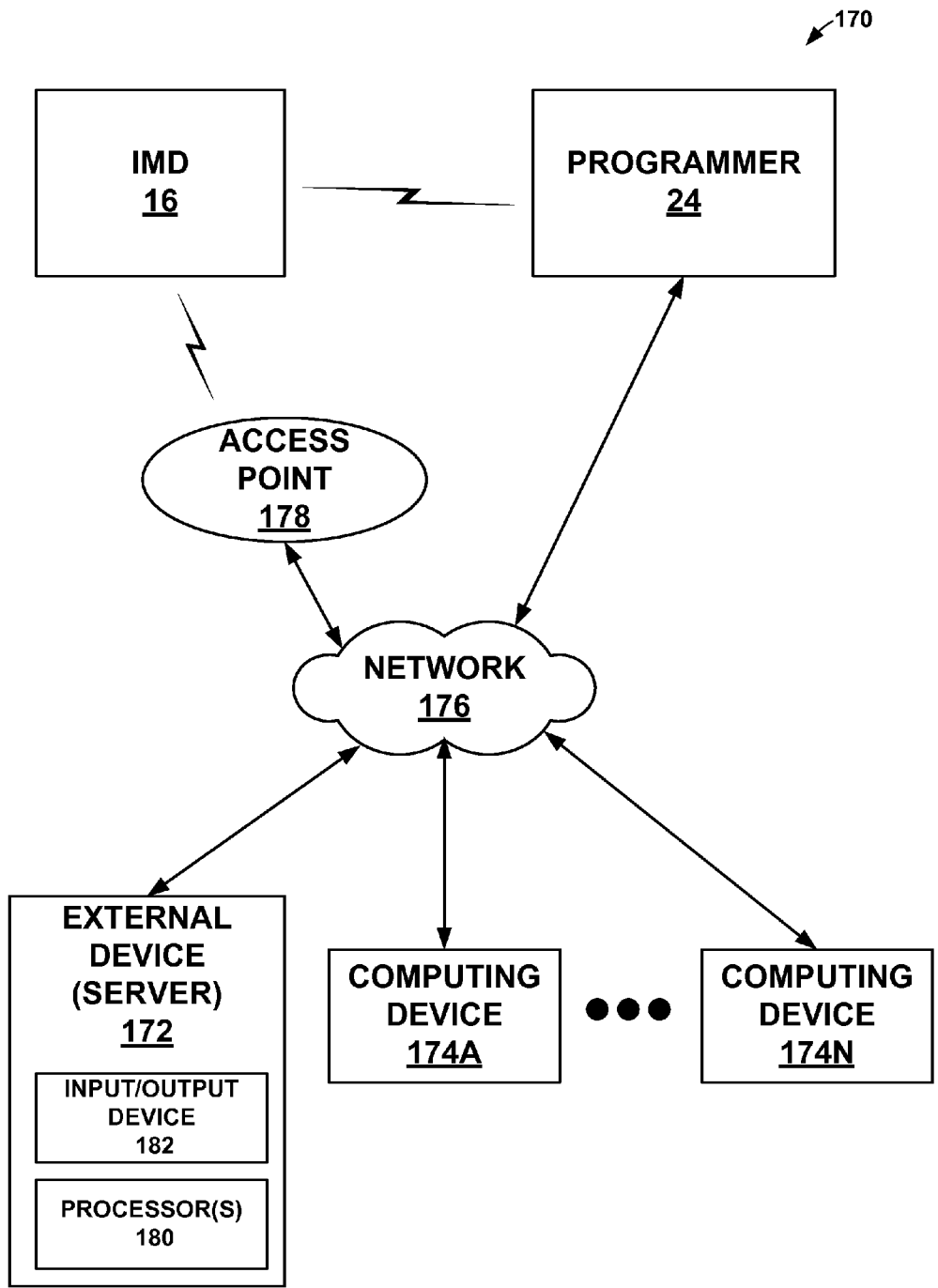
FIG. 14 is a block diagram illustrating an example system that includes an external device, such as a server, and one or more computing devices that are coupled to the IMD and programmer shown in FIG. 1 via a network.

FIG. 14 is a block diagram illustrating a system 170 that includes an external device 172, such as a server, and one or more computing devices 174A-174N that are coupled to IMD 16 and programmer 24 shown in FIG. 1 via a network 176, according to one example. In this example, IMD 16 uses its telemetry module 88 (FIG. 3) to communicate with programmer 24 via a first wireless connection, and to communicate with an access point 178 via a second wireless connection. In the example of FIG. 14, access point 178, programmer 24, external device 172, and computing devices 174A-174N are interconnected, and able to communicate with each other, through network 176. In some cases, one or more of access point 178, programmer 24, external device 172, and computing devices 174A-174N may be coupled to network 176 through one or more wireless connections. IMD 16, programmer 24, external device 172, and computing devices 174A-174N may each comprise one or more processors, such as one or more microprocessors, DSPs, ASICs, FPGAs, programmable logic circuitry, or the like, that may perform various functions and operations, such as those described herein.

Access point 178 may comprise a device that connects to network 176 via any of a variety of connections, such as telephone dial-up, digital subscriber line (DSL), or cable modem connections. In other examples, access point 178 may be coupled to network 176 through different forms of connections, including wired or wireless connections. In some examples, access point 178 may communicate with programmer 24 and/or IMD 16. Access point 178 may be co-located with patient 14 (e.g., within the same room or within the same site as patient 14) or may be remotely located from patient 14. For example, access point 178 may be a home monitor that is located in the patient's home or is portable for carrying with patient 14.

During operation, IMD 16 may collect, measure, and store various forms of diagnostic data. For example, as described previously, IMD 16 may collect ECG and/or EGM signals, determine different fusion pacing intervals, and determine different $A_{P/S}$–$RV_S$ intervals. In certain cases, IMD 16 may directly analyze collected diagnostic data and generate any corresponding reports or alerts. In some cases, however, IMD 16 may send diagnostic data to programmer 24, access point 178, and/or external device 172, either wirelessly or via access point 178 and network 176, for remote processing and analysis.

For example, IMD 16 may send programmer 24 data that indicates whether a loss of intrinsic AV conduction was detected. Programmer 24 may generate reports or alerts after analyzing the data. As another example, IMD 16 may send programmer 24, external device 172, or both a plurality of determined $A_{P/S}$–$RV_S$ intervals for, and programmer 24, external device 172, or both, may determine whether $A_{P/S}$–$RV_S$ intervals over time are increasing, thereby indicating a change in pacing configuration may be desirable. As another example, IMD 16 may send a system integrity indication generated by processor 80 (FIG. 3) to programmer 24, which may take further steps to determine whether there may be a possible condition with one or more of leads 18, 20, and 22. For example, programmer 24 may initiate lead impedance tests or IMD 16 may provide lead impedance information, if such information is already available.

In another example, IMD 16 may provide external device 172 with collected EGM data, system integrity indications, and any other relevant physiological or system data via access point 178 and network 176. External device 172 includes one or more processors 180. In some cases, external device 172 may request such data, and in some cases, IMD 16 may automatically or periodically provide such data to external device 172. Upon receipt of the diagnostic data via input/output device 182, external device 172 is capable of analyzing the data and generating reports or alerts upon determination that there may be a possible condition with one or more of leads 18, 20, and 22 or with patient 14.

In one example, external device 172 may comprise a secure storage site for information that has been collected from IMD 16 and/or programmer 24. In this example, network 176 may comprise an Internet network, and trained professionals, such as clinicians, may use computing devices 174A-174N to securely access stored data on external device 172. For example, the trained professionals may need to enter usernames and passwords to access the stored information on external device 172. In one embodiment, external device 172 may be a CareLink server provided by Medtronic, Inc., of Minneapolis, Minn.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system comprising:
   an electrical stimulation module configured to deliver cardiac resynchronization pacing therapy to a heart of a patient;
   a sensing module; and
   a processor configured to control the electrical stimulation module to deliver a pacing stimulus to a first ventricle of the heart, and determine whether a surrogate indication of intrinsic conduction from an atrium of the heart of the patient is detected after the electrical stimulation module delivers the pacing stimulus to the first ventricle, the processor being configured to determine whether the surrogate indication of the intrinsic conduction from the atrium is detected by at least determining whether the sensing module detected activation of a second ventricle of the heart within a predetermined window of time immediately following delivery of the pacing stimulus to the first ventricle by the electrical stimulation module, and the processor being further configured to control the cardiac resynchronization therapy delivered by the electrical stimulation module to the patient based on whether the surrogate indication of intrinsic conduction is detected after the electrical stimulation module delivers the pacing stimulus to the first ventricle,
   wherein the processor is configured to determine whether the surrogate indication of intrinsic conduction from the atrium of the heart to the second ventricle of the heart of the patient is detected by at least:
      determining an intrinsic atrioventricular (AV) conduction time measurement;
      determining an interval of time between an atrial pace or sense event and the activation of the second ventricle sensed via the sensing module;
      determining whether the interval of time is substantially equal to the intrinsic AV conduction time measurement;
      determining the surrogate indication of intrinsic conduction is detected in response to determining the interval of time is substantially equal to the intrinsic AV conduction time measurement; and
      determining the surrogate indication of intrinsic conduction is not detected in response determining the interval of time is not substantially equal to the intrinsic AV conduction time measurement.

2. A system comprising:
an electrical stimulation module configured to deliver cardiac resynchronization pacing therapy to a heart of a patient;
a sensing module; and
a processor configured to control the electrical stimulation module to deliver a pacing stimulus to a first ventricle of the heart, and determine whether a surrogate indication of intrinsic conduction from an atrium of the heart of the patient is detected after the electrical stimulation module delivers the pacing stimulus to the first ventricle, the processor being configured to determine whether the surrogate indication of the intrinsic conduction from the atrium is detected by at least determining whether the sensing module detected activation of a second ventricle of the heart within a predetermined window of time immediately following delivery of the pacing stimulus to the first ventricle by the electrical stimulation module, and the processor being further configured to control the cardiac resynchronization therapy delivered by the electrical stimulation module to the patient based on whether the surrogate indication of intrinsic conduction is detected after the electrical stimulation module delivers the pacing stimulus to the first ventricle,
wherein the processor is configured to control the electrical stimulation module to deliver the pacing stimulus to the first ventricle by at least:
  setting a first pacing interval and a second pacing interval;
  performing one of delivering a first atrial pace event or sensing a first atrial sense event; and
  controlling the electrical stimulation module to deliver a first pacing stimulus after expiration of the first pacing interval from the first atrial pace or sense event, and
  wherein the processor is configured to determine whether the surrogate indication of intrinsic conduction from the atrium of the heart to the second ventricle of the heart of the patient is detected by at least:
  detecting, based on electrical cardiac activity sensed by the sensing module, a first activation of the second ventricle within the predetermined window of time immediately following delivery of the first pacing stimulus to the first ventricle;
  determining a first time interval between the first pacing stimulus and the first activation of the second ventricle;
  performing one of delivering a second atrial pace event or sensing a second atrial sense event;
  controlling the electrical stimulation module to deliver a second pacing stimulus to the first ventricle after expiration of the second pacing interval from the second atrial pace or sense event, wherein the second pacing interval is less than the first pacing interval;
  detecting, based on electrical cardiac activity sensed by the sensing module, a second activation of the second ventricle within the predetermined window of time immediately following delivery of the second pacing stimulus to the first ventricle;
  determining a second time interval between the second pacing stimulus and the second activation of the second ventricle;
  determining the surrogate indication of intrinsic conduction is detected in response to determining the second time interval is greater than the first time interval; and
  determining the surrogate indication of intrinsic conduction is not detected in response to determining the second time interval is not greater than the first time interval.

3. A system comprising:
an electrical stimulation module configured to deliver cardiac resynchronization pacing therapy to a heart of a patient;
a sensing module; and
a processor configured to control the electrical stimulation module to deliver a pacing stimulus to a first ventricle of the heart, and determine whether a surrogate indication of intrinsic conduction from an atrium of the heart of the patient is detected after the electrical stimulation module delivers the pacing stimulus to the first ventricle, the processor being configured to determine whether the surrogate indication of the intrinsic conduction from the atrium is detected by at least determining whether the sensing module detected activation of a second ventricle of the heart within a predetermined window of time immediately following delivery of the pacing stimulus to the first ventricle by the electrical stimulation module, and the processor being further configured to control the cardiac resynchronization therapy delivered by the electrical stimulation module to the patient based on whether the surrogate indication of intrinsic conduction is detected after the electrical stimulation module delivers the pacing stimulus to the first ventricle,
wherein the processor is configured to:
  set a pacing interval,
  perform one of control the stimulation module to deliver an atrial pace event or identify an atrial sense event sensed by the sensing module; control the electrical stimulation module to deliver the pacing stimulus to the first ventricle of the heart by at least detecting one of the atrial pace or the atrial sense event and controlling the electrical stimulation module to deliver the pacing stimulus to the first ventricle after expiration of the pacing interval from the atrial pace or sense event, and wherein the processor is further configured to, after detecting the surrogate indication, determine a time interval between the atrial pace or sense event and the activation of the second ventricle, and adjust the pacing interval based on the time interval.

4. A system comprising:
an electrical stimulation module configured to deliver cardiac resynchronization pacing therapy to a heart of a patient;
a sensing module; and
a processor configured to control the electrical stimulation module to deliver a pacing stimulus to a first ventricle of the heart, and determine whether a surrogate indication of intrinsic conduction from an atrium of the heart of the patient is detected after the electrical stimulation module delivers the pacing stimulus to the first ventricle, the processor being configured to determine whether the surrogate indication of the intrinsic conduction from the atrium is detected by at least determining whether the sensing module detected activation of a second ventricle of the heart within a predetermined window of time immediately following delivery of the pacing stimulus to the first ventricle by the electrical stimulation module, and the processor being further configured to control the cardiac resynchronization therapy delivered by the electrical stimulation module to the patient based on whether the surrogate indication of intrinsic conduction is detected after the electrical stimulation module delivers the pacing stimulus to the first ventricle,
wherein the processor is configured to adjust the pacing interval based on the time interval by at least determining an adjusted pacing interval by at least decrementing the time interval by a predetermined pre-excitation interval.

5. A system comprising:
an electrical stimulation module configured to deliver cardiac resynchronization pacing therapy to a heart of a patient;
a sensing module; and
a processor configured to control the electrical stimulation module to deliver a pacing stimulus to a first ventricle of the heart, and determine whether a surrogate indication of intrinsic conduction from an atrium of the heart of the patient is detected after the electrical stimulation module delivers the pacing stimulus to the first ventricle, the processor being configured to determine whether the surrogate indication of the intrinsic conduction from the atrium is detected by at least determining whether the sensing module detected activation of a second ventricle of the heart within a predetermined window of time immediately following delivery of the pacing stimulus to the first ventricle by the electrical stimulation module, and the processor being further configured to control the cardiac resynchronization therapy delivered by the electrical stimulation module to the patient based on whether the surrogate indication of intrinsic conduction is detected after the electrical stimulation module delivers the pacing stimulus to the first ventricle,
wherein the processor is configured to adjust the pacing interval based on the time interval once per cardiac cycle of the heart.

6. A method comprising:
controlling an electrical stimulation module to deliver a pacing stimulus to a first ventricle of a heart of a patient;
after the electrical stimulation module delivers the pacing stimulus to the first ventricle, determining with a processor, whether a surrogate indication of intrinsic conduction from an atrium of the heart of the patient is detected, wherein determining whether the surrogate indication of the intrinsic conduction is detected comprises detecting activation of a second ventricle of the heart within a predetermined window of time immediately following delivery of the pacing stimulus to the first ventricle; and
with the processor, controlling cardiac resynchronization therapy delivered by the electrical stimulation module to the patient based on whether the surrogate indication of intrinsic conduction is detected,
wherein determining whether the surrogate indication of intrinsic conduction from the atrium of the heart to the second ventricle of the heart of the patient is detected further comprises:
determining a time interval between an atrial pace or sense event and the activation of the second ventricle;
determining whether the time interval is substantially equal to an intrinsic conduction time measurement;
determining the surrogate indication of intrinsic conduction is detected in response to determining the time interval is substantially equal to the intrinsic conduction time measurement; and
determining the surrogate indication of intrinsic conduction is not detected in response to determining the time interval is substantially not equal to the intrinsic conduction time measurement.

7. A method comprising:
controlling an electrical stimulation module to deliver a pacing stimulus to a first ventricle of a heart of a patient;
after the electrical stimulation module delivers the pacing stimulus to the first ventricle, determining with a processor, whether a surrogate indication of intrinsic conduction from an atrium of the heart of the patient is detected, wherein determining whether the surrogate indication of the intrinsic conduction is detected comprises detecting activation of a second ventricle of the heart within a predetermined window of time immediately following delivery of the pacing stimulus to the first ventricle; and
with the processor, controlling cardiac resynchronization therapy delivered by the electrical stimulation module to the patient based on whether the surrogate indication of intrinsic conduction is detected,
wherein controlling the electrical stimulation module to deliver the pacing stimulus to the first ventricle comprises:
detecting a first atrial pace or sense event; and
controlling the electrical stimulation module to deliver a first pacing stimulus after expiration of a first pacing interval from the first atrial pace or sense event, and
wherein determining whether the surrogate indication of intrinsic conduction from the atrium of the heart to the second ventricle of the heart of the patient is detected comprises:
detecting a first activation of the second ventricle within the predetermined window of time immediately following delivery of the first pacing stimulus to the first ventricle;
determining a first time interval between the first pacing stimulus and the first activation of the second ventricle;
detecting a second atrial pace or sense event;
controlling the electrical stimulation module to deliver a second pacing stimulus to the first ventricle after expiration of a second pacing interval from the second atrial pace or sense event, wherein the second pacing interval is less than the first pacing interval;
detecting a second activation of the second ventricle within the predetermined window of time immediately following delivery of the second pacing stimulus to the first ventricle
determining a second time interval between the second pacing stimulus and the second activation of the second ventricle;
determining the surrogate indication of intrinsic conduction is detected in response to determining the second time interval is greater than the first time interval; and
determining the surrogate indication of intrinsic conduction is not detected in response to determining the second time interval is not greater than the first time interval.

8. A method comprising:
controlling an electrical stimulation module to deliver a pacing stimulus to a first ventricle of a heart of a patient;
after the electrical stimulation module delivers the pacing stimulus to the first ventricle, determining with a processor, whether a surrogate indication of intrinsic conduction from an atrium of the heart of the patient is detected, wherein determining whether the surrogate indication of the intrinsic conduction is detected comprises detecting activation of a second ventricle of the heart within a predetermined window of time immediately following delivery of the pacing stimulus to the first ventricle; and
with the processor, controlling cardiac resynchronization therapy delivered by the electrical stimulation module to the patient based on whether the surrogate indication of intrinsic conduction is detected,
wherein controlling the electrical stimulation module to deliver the pacing stimulus to the first ventricle of the heart comprises:

detecting an atrial pace or sense event; and
controlling the electrical stimulation module to deliver the pacing stimulus to the first ventricle after expiration of a pacing interval from the atrial pace or sense event, and wherein the method further comprises, after determining the surrogate indication is detected:
determining a time interval between the atrial pace or sense event and the activation of the second ventricle;
adjusting the pacing interval based on the time interval.

9. A method comprising:
controlling an electrical stimulation module to deliver a pacing stimulus to a first ventricle of a heart of a patient;
after the electrical stimulation module delivers the pacing stimulus to the first ventricle, determining with a processor, whether a surrogate indication of intrinsic conduction from an atrium of the heart of the patient is detected, wherein determining whether the surrogate indication of the intrinsic conduction is detected comprises detecting activation of a second ventricle of the heart within a predetermined window of time immediately following delivery of the pacing stimulus to the first ventricle; and
with the processor, controlling cardiac resynchronization therapy delivered by the electrical stimulation module to the patient based on whether the surrogate indication of intrinsic conduction is detected wherein controlling the electrical stimulation module to deliver the pacing stimulus to the first ventricle of the heart comprises:
detecting an atrial pace or sense event; and
controlling the electrical stimulation module to deliver the pacing stimulus to the first ventricle after expiration of a pacing interval from the atrial pace or sense event, and wherein the method further comprises, after determining the surrogate indication is detected:
determining a time interval between the atrial pace or sense event and the activation of the second ventricle;
adjusting the pacing interval based on the time interval,
wherein adjusting the pacing interval based on the time interval comprises determining an adjusted pacing interval by at least decrementing the time interval by a predetermined pre-excitation interval.

10. A method comprising:
controlling an electrical stimulation module to deliver a pacing stimulus to a first ventricle of a heart of a patient,
after the electrical stimulation module delivers the pacing stimulus to the first ventricle, determining with a processor, whether a surrogate indication of intrinsic conduction from an atrium of the heart of the patient is detected, wherein determining whether the surrogate indication of the intrinsic conduction is detected comprises detecting activation of a second ventricle of the heart within a predetermined window of time immediately following delivery of the pacing stimulus to the first ventricle; and
with the processor, controlling cardiac resynchronization therapy delivered by the electrical stimulation module to the patient based on whether the surrogate indication of intrinsic conduction is detected wherein controlling the electrical stimulation module to deliver the pacing stimulus to the first ventricle of the heart comprises:
detecting an atrial pace or sense event; and
controlling the electrical stimulation module to deliver the pacing stimulus to the first ventricle after expiration of a pacing interval from the atrial pace or sense event and wherein the method further comprises, after determining the surrogate indication is detected:
determining a time interval between the atrial pace or sense event and the activation of the second ventricle;
adjusting the pacing interval based on the time interval,
wherein adjusting the pacing interval based on the time interval comprises adjusting the pacing interval once per cardiac cycle of the heart.

11. A system comprising:
means for delivering cardiac resynchronization therapy to a heart of a patient;
means for determining whether a surrogate indication of intrinsic conduction from an atrium of the heart is detected after the means for delivering cardiac resynchronization therapy delivers a pacing stimulus to a first ventricle of the heart,
wherein the means for determining whether the surrogate indication of intrinsic conduction is detected comprises means for detecting activation of a second ventricle of the heart within a predetermined window of time immediately following delivery of the pacing stimulus to the first ventricle; and
means for controlling cardiac resynchronization therapy delivered by the means for delivering cardiac resynchronization therapy based on whether the surrogate indication of intrinsic conduction is detected, further comprising means for sensing atrial sense event;
wherein the means for controlling cardiac resynchronization therapy is configured to set a pacing interval and control the means for delivering cardiac resynchronization therapy to deliver the pacing stimulus to the first ventricle of the heart by at least one of controlling the means for delivering to deliver an atrial pace event or detecting an atrial sense event sensed by the means for sensing and delivering the pacing stimulus to the first ventricle after expiration of the pacing interval from the atrial pace or sense event, the system further comprising:
means for determining a time interval between the atrial pace or sense event and the activation of the second ventricle if the surrogate indication of intrinsic conduction is detected; and
means for adjusting the pacing interval based on the time interval.

12. A non-transitory computer-readable medium comprising instructions that, when executed by a processor, cause the processor to:
control an electrical stimulation module to deliver a pacing stimulus to a first ventricle of a heart of a patient;
after the medical device delivers the pacing stimulus to the first ventricle, determine whether a surrogate indication of intrinsic conduction of the heart of the patient is detected, wherein the instructions cause the processor to determine whether the surrogate indication of the intrinsic conduction is detected by at least detecting activation of a second ventricle of the heart within a predetermined window of time immediately following delivery of the pacing stimulus to the first ventricle; and
control cardiac resynchronization therapy delivered by the electrical stimulation module to the patient based on whether the surrogate indication of intrinsic conduction of the heart of the patient is detected,
further comprising instructions that, when executed by the processor, cause the processor to:
determine a time interval between an atrial pace or sense event and the activation of the second ventricle if the surrogate indication of intrinsic conduction is detected; and adjust a pacing interval with which the electrical stimulation module delivers pacing stimuli to the first ventricle of the heart based on the time interval.

\* \* \* \* \*